US008048124B2

(12) United States Patent
Chin et al.

(10) Patent No.: US 8,048,124 B2
(45) Date of Patent: Nov. 1, 2011

(54) SPINAL SCREW ASSEMBLY AND SCREW INSERTION TOOL

(75) Inventors: Kingsley R. Chin, Riviera Beach, FL (US); Christopher Chang, Beverly, MA (US); Ernie Corrao, Bethel, CT (US); Todd Saunders, Boston, MA (US); Stephen Santangelo, Wallington, CT (US)

(73) Assignee: Spinefrontier Inc, Beverly, MA (US)

( * ) Notice: Subject to any disclaimer, the term of this patent is extended or adjusted under 35 U.S.C. 154(b) by 301 days.

(21) Appl. No.: 12/558,046

(22) Filed: Sep. 11, 2009

(65) Prior Publication Data

US 2010/0063552 A1 Mar. 11, 2010

Related U.S. Application Data

(63) Continuation-in-part of application No. 11/121,414, filed on May 4, 2005, now Pat. No. 7,811,310.

(60) Provisional application No. 61/097,288, filed on Sep. 16, 2008.

(51) Int. Cl.
*A61B 17/70* (2006.01)

(52) U.S. Cl. ........ 606/264; 606/265; 606/267; 606/300; 606/305

(58) Field of Classification Search .................. 606/104, 606/264–278, 300–321; 411/337–350, 352–353, 411/367–370, 366.1–366.3, 372.5
See application file for complete search history.

(56) References Cited

U.S. PATENT DOCUMENTS

| | | | |
|---|---|---|---|
| 6,077,262 | A | 6/2000 | Schlapfer et al. |
| 6,547,789 | B1 | 4/2003 | Ventre et al. |
| 7,081,117 | B2 | 7/2006 | Bono et al. |
| 7,125,426 | B2 | 10/2006 | Moumene et al. |
| 2007/0032162 | A1 | 2/2007 | Jackson |
| 2007/0288004 | A1 | 12/2007 | Alvarez |
| 2008/0221583 | A1 | 9/2008 | Sharifi-Mehr et al. |
| 2008/0275456 | A1 | 11/2008 | Vonwiller et al. |
| 2009/0005787 | A1 | 1/2009 | Crall et al. |

*Primary Examiner* — Eduardo C Robert
*Assistant Examiner* — Christina Negrelli
(74) *Attorney, Agent, or Firm* — AKC Patents LLC; Aliki K. Collins

(57) ABSTRACT

A bone screw assembly includes a tulip-shaped seat, a bone fixation device, a ring-shaped washer, a rod and a cap. The tulip-shaped seat comprises a through opening dimensioned to receive the bone fixation device and a horizontal channel dimensioned to receive the rod. The washer is placed into the seat on top of the bone fixation device head and comprises first and second side tabs and a first pair of upward extending projections separated by a first gap and a second pair of upward extending projections separated by a second gap. The side tabs interface with a groove formed in the bottom portion of the seat. The rod is placed within the channel and positioned within a groove formed on the top surface of the washer. The cap includes first and second projections extending downward from its bottom surface and each of the first and second downward projections comprises first and second sidewise extending ridges. The first ridges of the first and second projections are aligned and placed within the first and second gaps of the washer, respectively, and interface with a first groove formed on the side portion of the seat and the second ridges interface with a second groove on the side portion of the seat when the cap is rotate.

15 Claims, 41 Drawing Sheets

SPINAL SCREW ASSEMBLY AND SCREW INSERTION TOOL

CROSS REFERENCE TO RELATED CO-PENDING APPLICATIONS

This application claims the benefit of U.S. provisional application Ser. No. 61/097,288 filed Sep. 16, 2008 and entitled "SPINAL SCREW ASSEMBLY", the contents of which are expressly incorporated herein by reference.

This application is also a continuation in part of U.S. application Ser. No. 11/121,414 filed on May 4, 2005 and entitled "MULTISTAGE SPINAL FIXATION LOCKING MECHANISM" the contents of which are expressly incorporated herein by reference.

FIELD OF THE INVENTION

The present invention relates to a spinal screw assembly and to a screw insertion tool, and in particular to a spinal screw assembly used in connection with spinal stabilization rods.

BACKGROUND OF THE INVENTION

The human spine comprises individual vertebras 30 (segments) that are connected to each other to form a spinal column 29, shown in FIG. 1A. Referring to FIGS. 1B and 1C, each vertebra 30 has a cylindrical bony body (vertebral body) 32, three winglike projections (two transverse processes 33, 35 and one spinous process 34), left and right facet joints 46, lamina 47, left and right pedicles 48 and a bony arch (neural arch) 36. The bodies of the vertebrae 32 are stacked one on top of the other and form the strong but flexible spinal column. The neural arches 36 are positioned so that the space they enclose forms a tube, i.e., the spinal canal 37. The spinal canal 37 houses and protects the spinal cord and other neural elements. A fluid filled protective membrane, the dura 38, covers the contents of the spinal canal. The spinal column is flexible enough to allow the body to twist and bend, but sturdy enough to support and protect the spinal cord and the other neural elements. The vertebras 30 are separated and cushioned by thin pads of tough, resilient fiber known as inter-vertebral discs 40. Disorders of the spine occur when one or more of the individual vertebras 30 and/or the inter-vertebral discs 40 become abnormal either as a result of disease or injury. In these pathologic circumstances, fusion of adjacent vertebral segments may be tried to restore the function of the spine to normal, achieve stability, protect the neural structures, or to relief the patient of discomfort.

Several spinal fixation systems exist for stabilizing the spine so that bony fusion is achieved. The majority of these fixation systems utilize rods that attach to screws which are threaded into the vertebral bodies or the pedicles. These systems can be extended along the sides of the spine by connecting two adjacent pedicles at a time similar to the concept of a bicycle chain. Spinal screw assemblies that allow support of stabilization rods without adding bulk to the lateral aspect of the spine or limiting access to the pars and transverse processes are desirable.

SUMMARY OF THE INVENTION

In general, in one aspect, the invention features a bone screw assembly including a tulip-shaped seat, a bone fixation device, a ring-shaped washer, a rod and a cap. The tulip-shaped seat comprises a semispherical bottom portion and a cylindrical side portion extending upward from the bottom portion. The bottom portion comprises a through opening dimensioned to receive the bone fixation device and to prevent the fixation device from passing entirely therethrough. The side portion comprises first and second concentric grooves extending along its inside periphery wall and a horizontal channel dimensioned to receive the rod. The bone fixation device comprises a bone fixation portion passing through the bottom portion opening and a head residing within the semispherical bottom portion. The ring-shaped washer is placed into the seat on top of the bone fixation device head and includes a first pair of outward extending projections separated by a first gap and a second pair of outward extending projections separated by a second gap. The projections extend from the top surface of the washer and are shaped and dimensioned to interface with the first concentric groove of the seat side portion. The rod placed within the channel and positioned within a groove formed on the top surface of the washer. The cap includes first and second projections extending downward from its bottom surface and wherein each of the first and second downward projections comprises first and second sidewise extending ridges and wherein the first ridges of the first and second projections are aligned and placed within the first and second gaps of the washer, respectively, and interface with the first groove of the seat side portion and the second ridges interface with the second groove of the seat side portion when the cap is rotate.

Implementations of this aspect of the invention may include one or more of the following features. The bone fixation device may be a polyaxial screw. The bone screw assembly may further include a locking screw threaded through a central opening formed in the cap for locking the rod down onto the bone fixation head.

In general in another aspect the invention features a bone screw assembly including a tulip-shaped seat, a ring-shaped washer, a rod and a cap. The tulip-shaped seat comprises a semispherical bottom portion, a cylindrical side portion extending upward from the bottom portion and a bone fixation device extending downward from the bottom portion. The side portion comprises first and second concentric grooves extending along its inside periphery wall and a horizontal channel dimensioned to receive the rod. The ring-shaped washer is placed into the seat on top of the head of the bone fixation device and comprises a first pair of outward extending projections separated by a first gap and a second pair of outward extending projections separated by a second gap. The projections extend from the top surface of the washer and are shaped and dimensioned to interface with the first concentric groove of the seat side portion. The rod is placed within the channel and positioned within a groove formed on the top surface of the washer. The cap comprises first and second projections extending downward from its bottom surface. Each of the first and second downward projections comprises first and second sidewise extending ridges. The first ridges of the first and second projections are aligned and placed within the first and second gaps of the washer, respectively, and interface with the first groove of the seat side portion and the second ridges interface with the second groove of the seat side portion when the cap is rotate.

In general, in another aspect, the invention features a bone screw assembly including a tulip-shaped seat, a bone fixation device, a cylindrically shaped washer, a rod and a cap. The tulip-shaped seat comprises a semispherical bottom portion and a cylindrical side portion extending upward from the bottom portion. The bottom portion comprises a through opening dimensioned to receive the bone fixation device and to prevent the fixation device from passing entirely therethrough. The side portion comprises first and second side through openings arranged opposite to each other and on opposite sides of the side portion and a horizontal channel dimensioned to receive the rod. The bone fixation device comprises a bone fixation portion passing through the bottom portion opening and a head residing within the semispherical bottom portion. The cylindrically shaped washer is placed into the seat on top of the bone fixation device head and comprises a first and second outward extending side projections. The side projections extend from the opposite sides of the washer side surface and are shaped and dimensioned to interface with the first and second side through openings of the seat, respectively and to protrude through the outer surface of the seat side portion. The rod is placed within the channel and positioned within a groove formed on the top surface of the washer. The cap comprises first and second sides extending downward from its bottom surface and the first and second sides comprise first and second grooves, respectively. The first and second grooves of the first and second sides are aligned and placed around the outer surface of the seat side portion, and interface with the first and second side projection protruding through the first and second side through openings when the cap is rotate.

In general, in another aspect, the invention features a bone screw assembly including a tulip-shaped seat, a bone fixation device, a cylindrically shaped washer, a rod and a cap. The tulip-shaped seat comprises a semispherical bottom portion and a cylindrical side portion extending upward from the bottom portion. The bottom portion comprises a groove extending along its inside periphery wall and a through opening dimensioned to receive the bone fixation device and to prevent the fixation device from passing entirely therethrough. The side portion comprises first and second concentric grooves extending along its inside periphery wall and a horizontal channel dimensioned to receive the rod. The bone fixation device comprises a bone fixation portion passing through the bottom portion opening and a head residing within the semispherical bottom portion. The washer is placed into the seat on top of the bone fixation device head and comprises first and second side tabs and a first pair of upward extending projections separated by a first gap and a second pair of upward extending projections separated by a second gap. The projections extend from the top surface of the washer and the first and second side tabs extend from opposite external sidewall of the washer and interface with the bottom portion groove. The rod is placed within the channel and positioned within a groove formed on the top surface of the washer. The cap comprises first and second projections extending downward from its bottom surface and each of the first and second downward projections comprises first and second sidewise extending ridges. The first ridges of the first and second projections are aligned and placed within the first and second gaps of the washer, respectively, and interface with the first groove of the side portion of the seat and the second ridges interface with the second groove of the side portion of the seat when the cap is rotate.

In general, in another aspect, the invention features an inserter tool for inserting a bone screw assembly. The bone screw assembly includes a bone screw and a tulip-shaped seat. The inserter tool includes a driver shaft, a retention sleeve, a spring and a pawl. The driver shaft comprises an elongated cylindrical body having a screw engaging distal end. The cylindrical body comprises upper and lower portions and the upper portion has a diameter larger than the diameter of the lower portion. The retention sleeve surrounds the driver shaft body and comprises a hollow cylindrical body having an upper portion, a lower portion and an intermediate step portion. The upper portion has a diameter larger than the diameter of the lower portion and is dimensioned to house the driver shaft upper portion and the lower portion is dimensioned to house the driver shaft lower portion. The retention sleeve lower portion comprises first and second flexible parallel segments. The spring surrounds the driver shaft upper portion and the driver shaft is configured to be pushed down or pulled up and slide within the retention sleeve and to compress the spring against the step portion. The pawl is configured to lock the position of the driver shaft relative to the retention sleeve. The first and second flexible segments comprise first and second distal ends, respectively, configured to engage the tulip-shaped seat.

Implementations of this aspect of the invention may include one or more of the following features. Each of the distal ends comprises a half annular ridge and first and second elongated protrusions extending downward from the bottom surface of the distal end. The annular ridge interfaces with an annular groove formed in the tulip-shaped seat and the first and second protrusions interface with the walls of a U-shaped opening formed in the tulip-shaped seat. The driver shaft lower portion comprises a diameter larger than the diameter of the lower portion of the retention sleeve and pushing the driver shaft down flexes the first and second flexible segments outward and locks the side annular ridges into the annular groove, thereby locking the tulip-shaped seat onto the first and second distal ends. The inserter tool may further comprise an outer sleeve surrounding the retention sleeve. The inserter tool may further comprise a handle.

The details of one or more embodiments of the invention are set forth in the accompanying drawings and description below. Other features, objects and advantages of the invention will be apparent from the following description of the preferred embodiments, the drawings and from the claims.

BRIEF DESCRIPTION OF THE DRAWINGS

Referring to the figures, wherein like numerals represent like parts throughout the several views.

DETAILED DESCRIPTION OF THE INVENTION

Figure 1A:
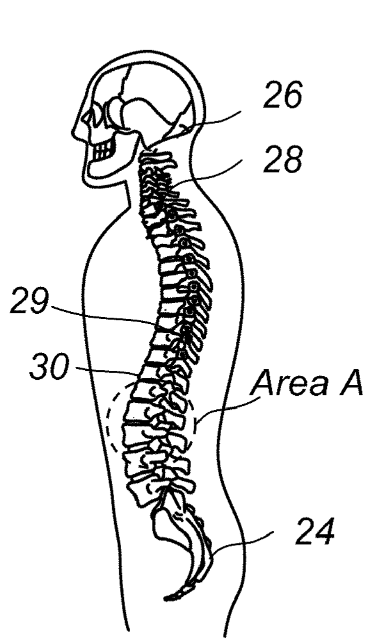
FIG. 1A is a side view of the human spinal column.
Figure 1B:
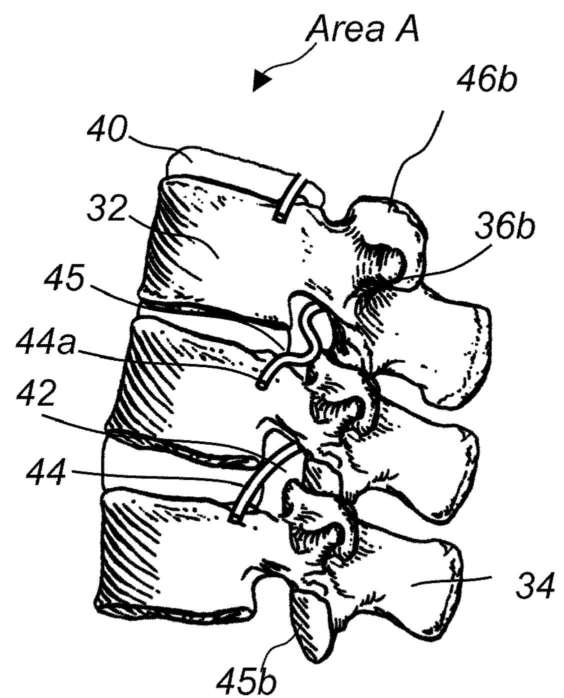
FIG. 1B is an enlarged view of area A of FIG. 1A.
Figure 1C:
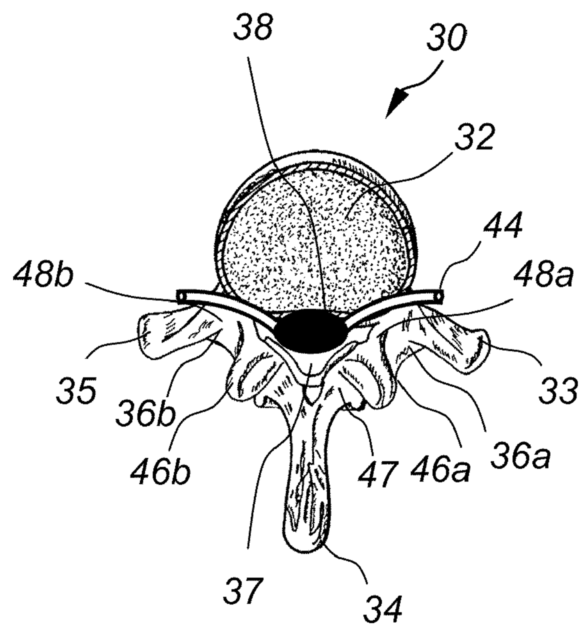
FIG. 1C is an axial cross-sectional view of a lumbar vertebra.
Figure 2:
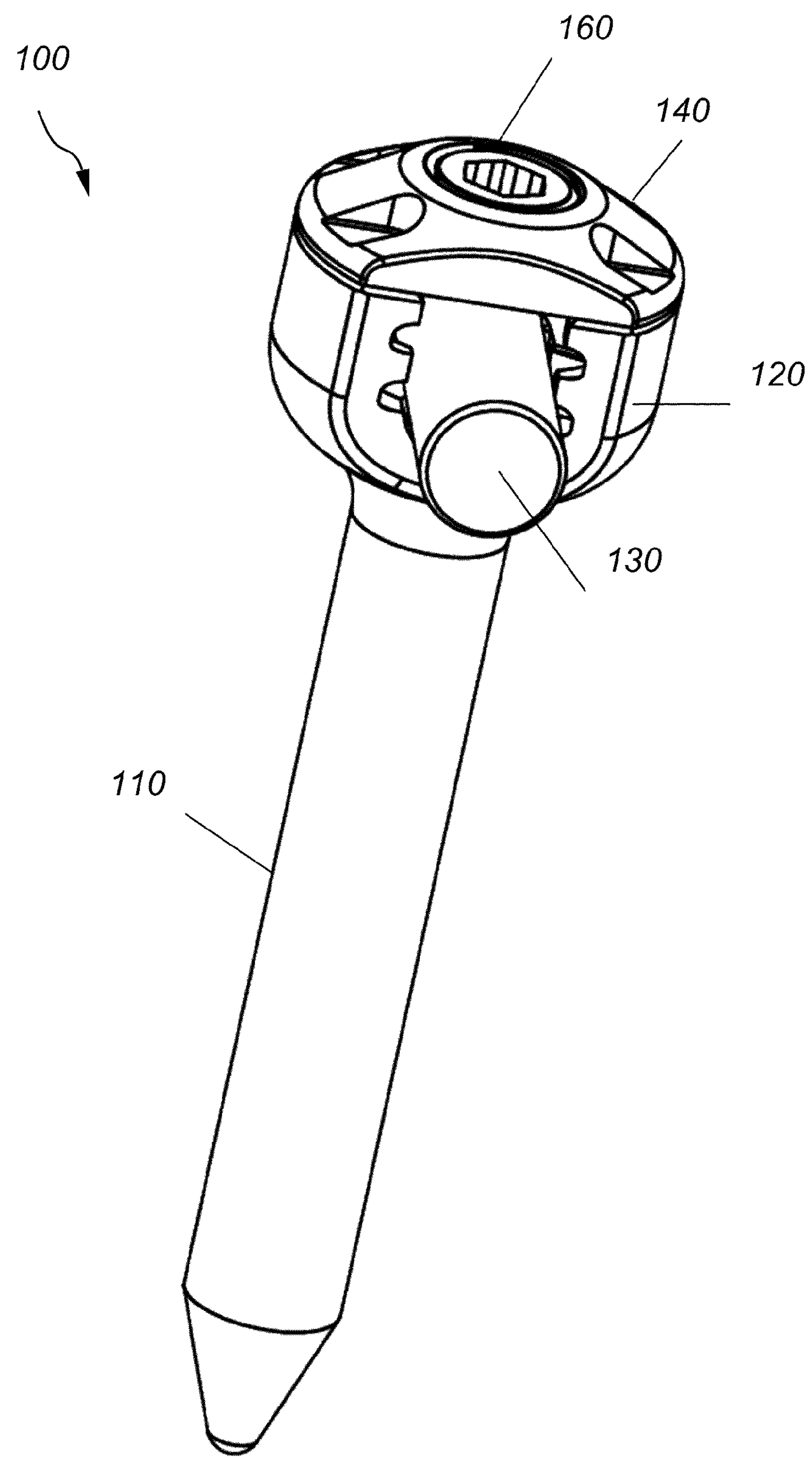
FIG. 2 is a front perspective view of a first embodiment of the spinal screw assembly.
Figure 3:
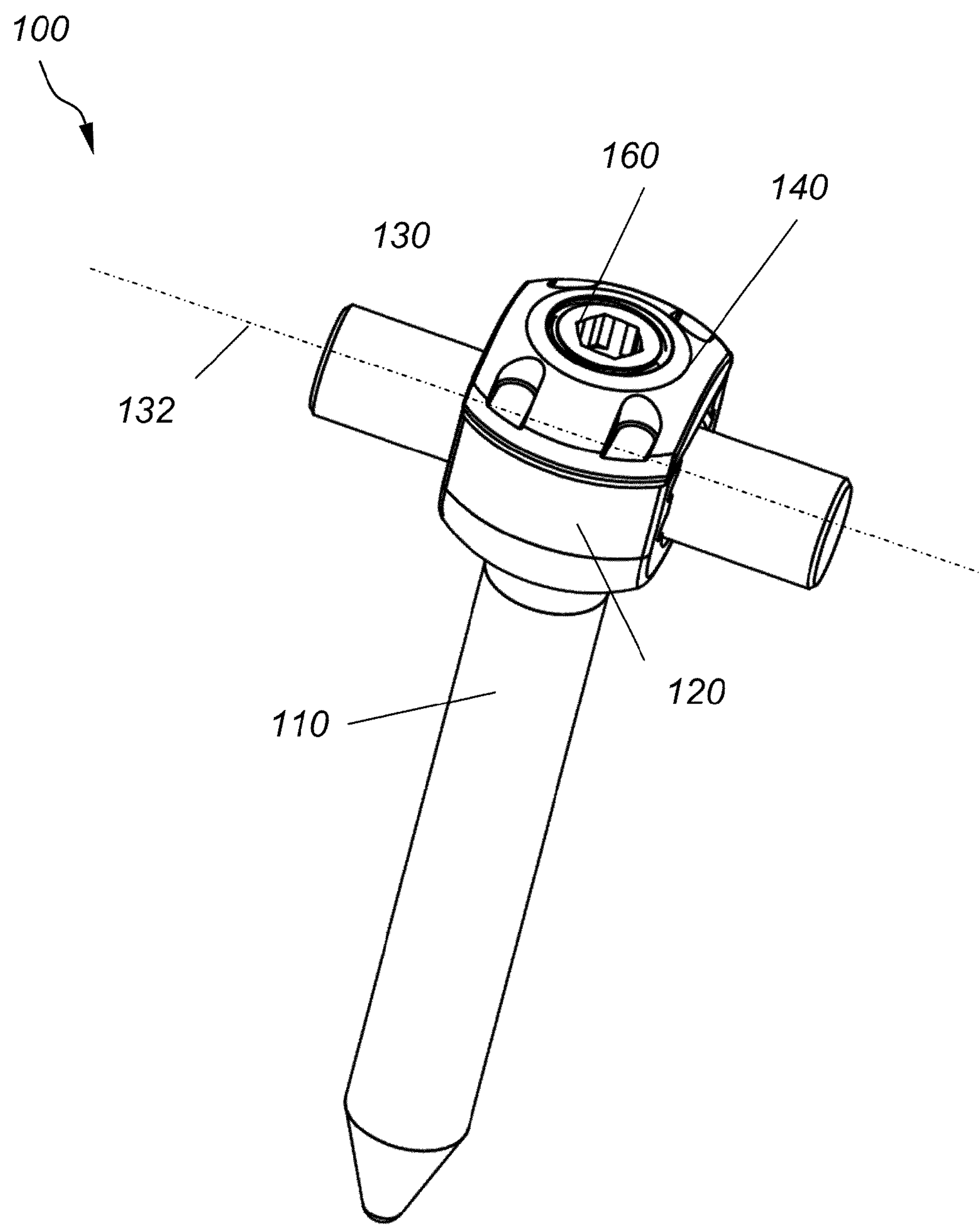
FIG. 3 is a side perspective view of the spinal screw assembly of FIG. 2.
Figure 4:
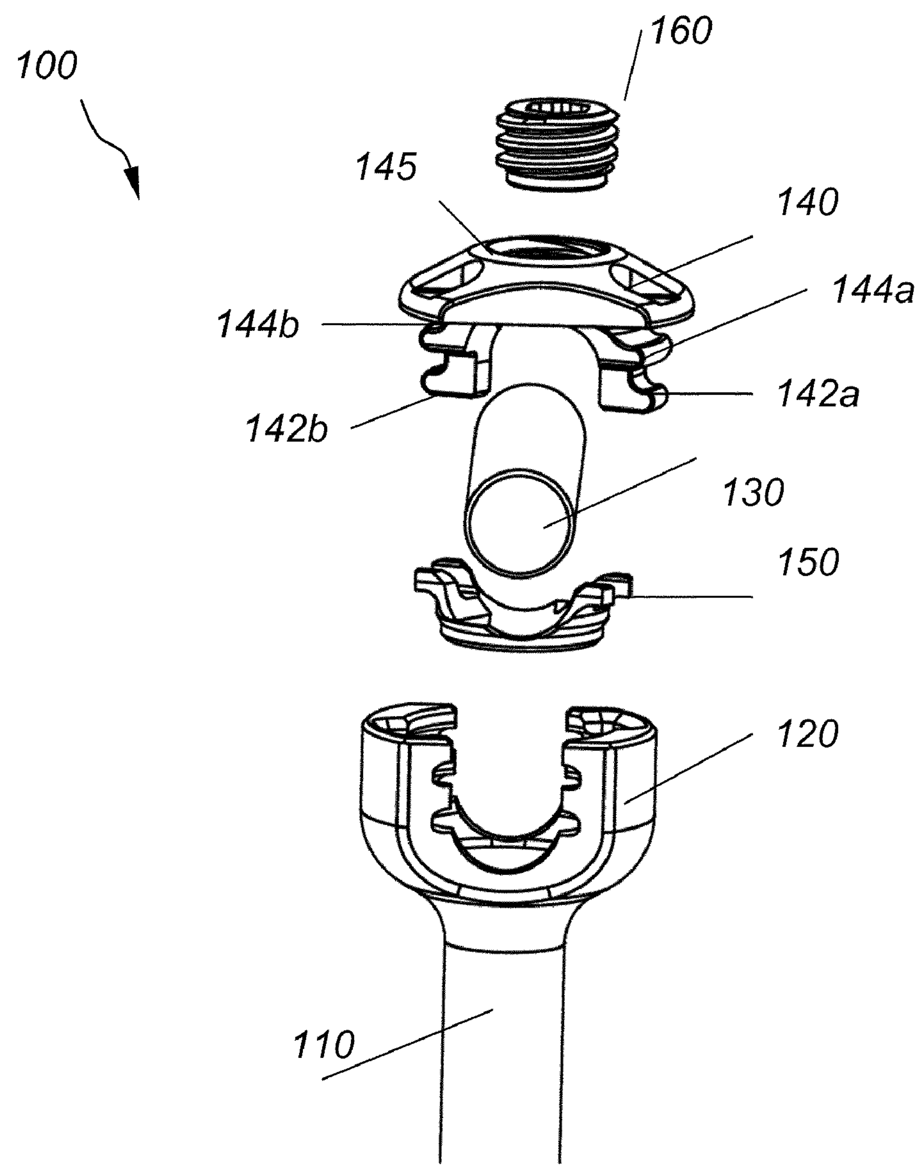
FIG. 4 is an exploded view of the spinal screw assembly of FIG. 2.
Figure 5:
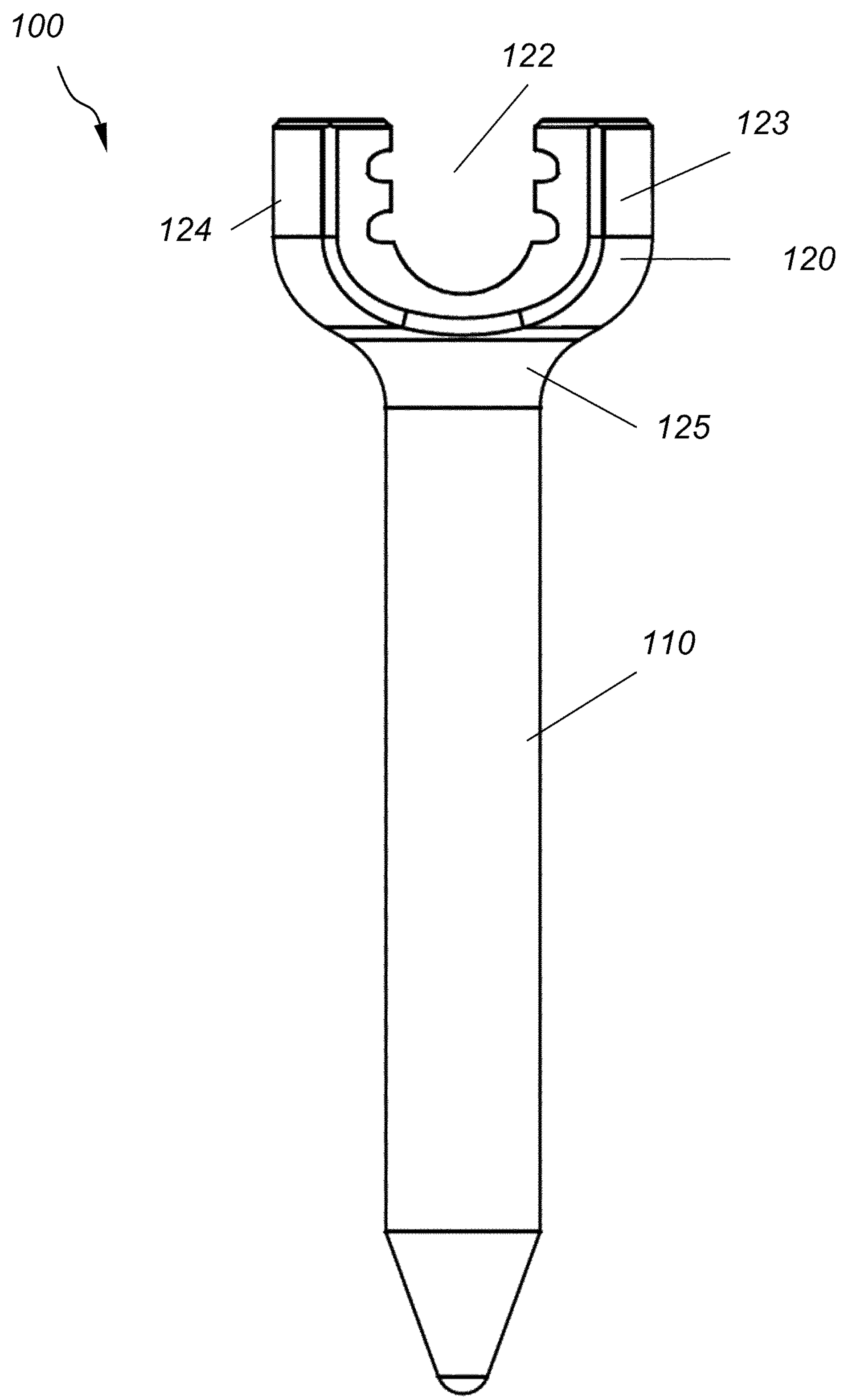
FIG. 5 is a side view of the anchoring portion and head of the spinal screw assembly of FIG. 2.
Figure 6:
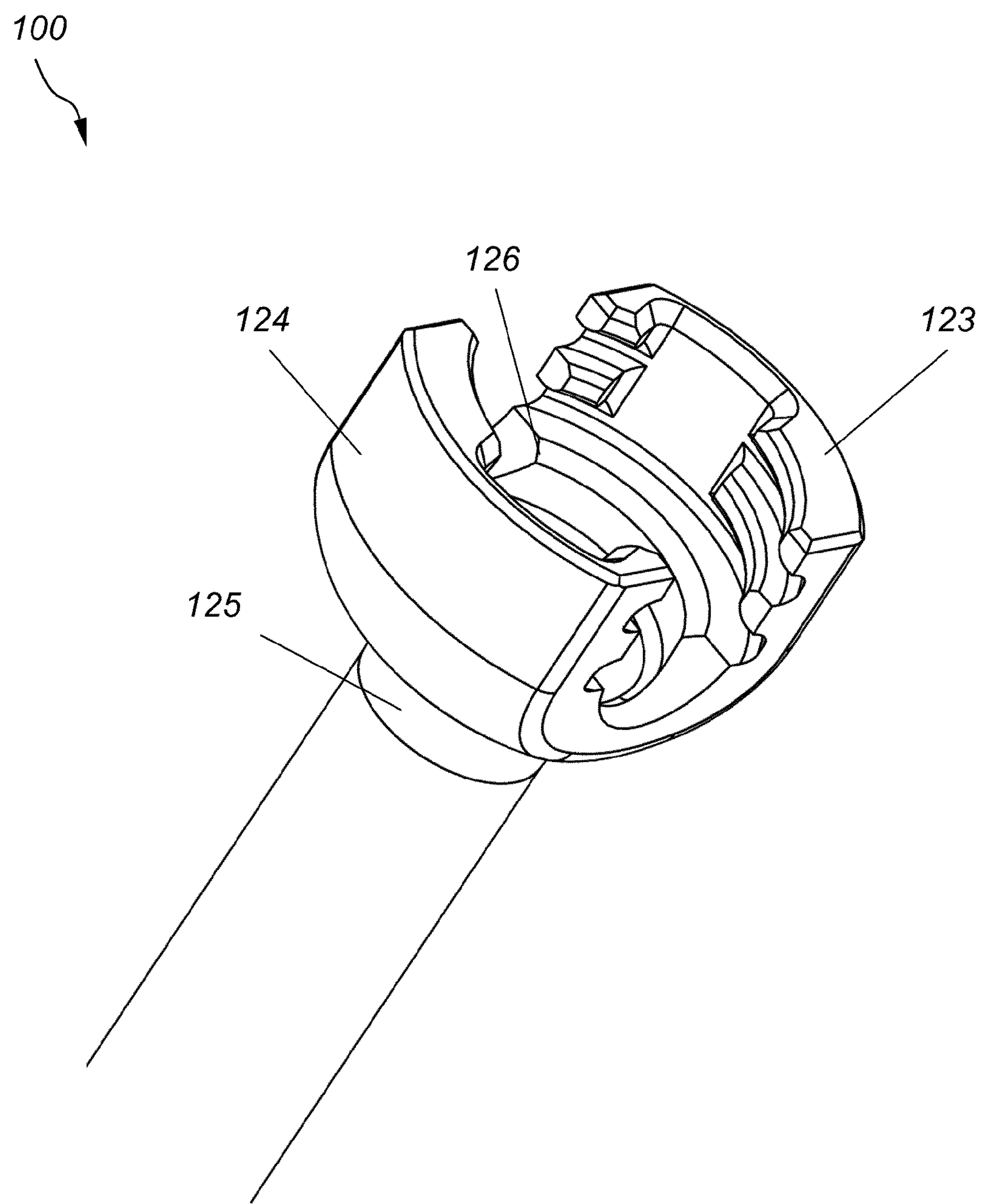
FIG. 6 is a top view of the head of FIG. 5.
Figure 7:
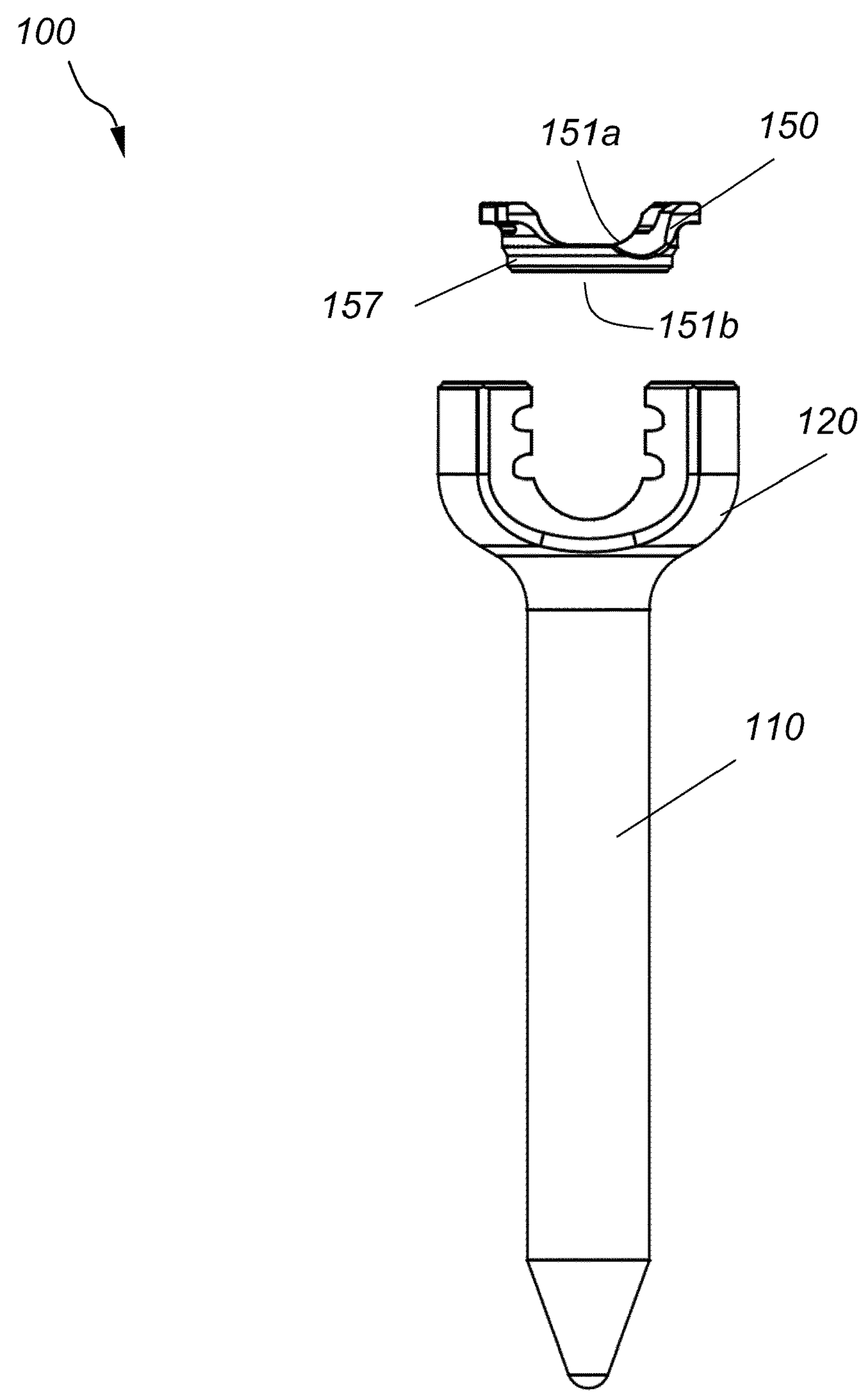
FIG. 7 is a side exploded view of the anchoring portion, head and washer of the spinal screw assembly of FIG. 2.
Figure 8:
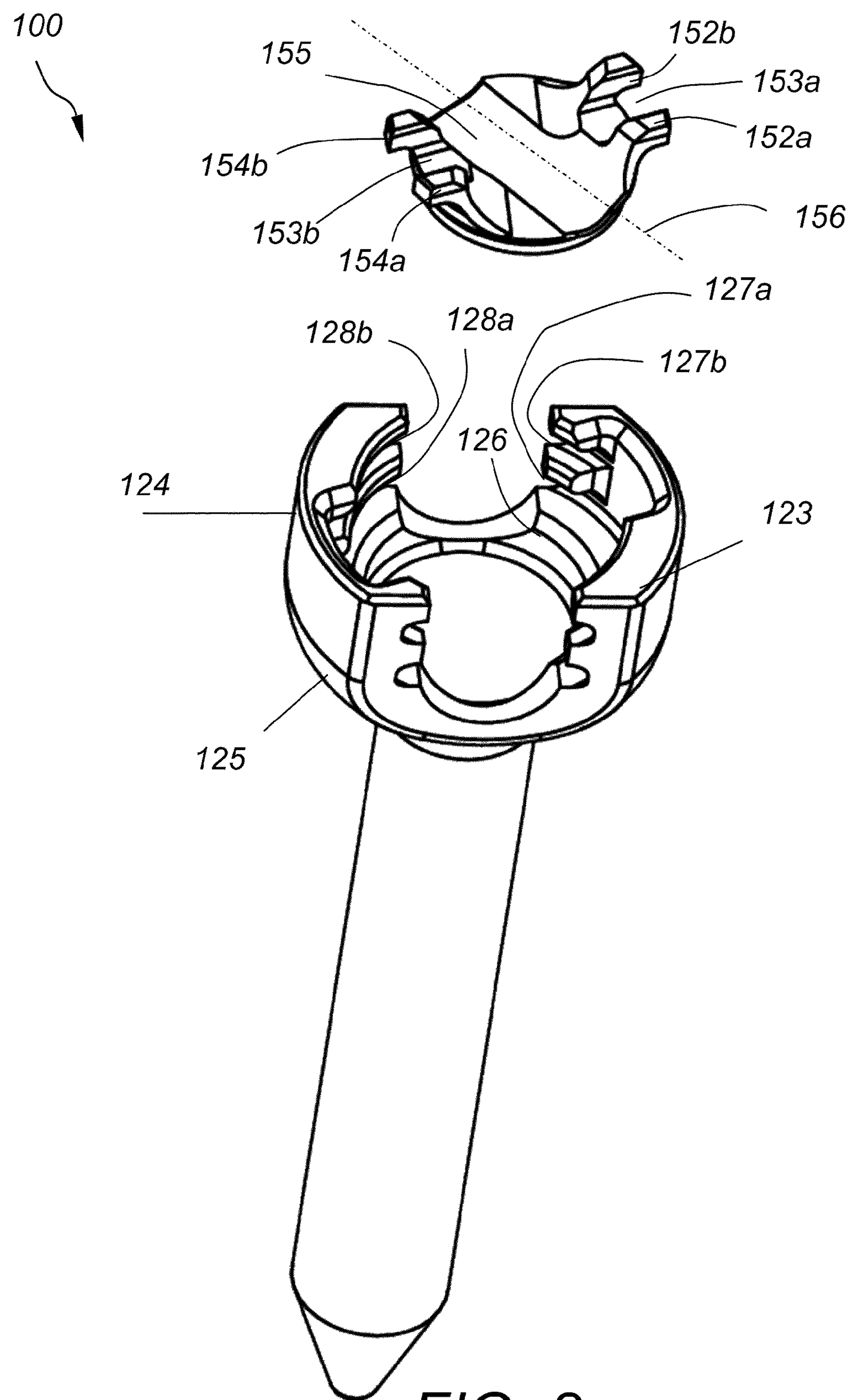
FIG. 8 is a top exploded view of the anchoring portion, head and washer of the spinal screw assembly of FIG. 2.
Figure 9:
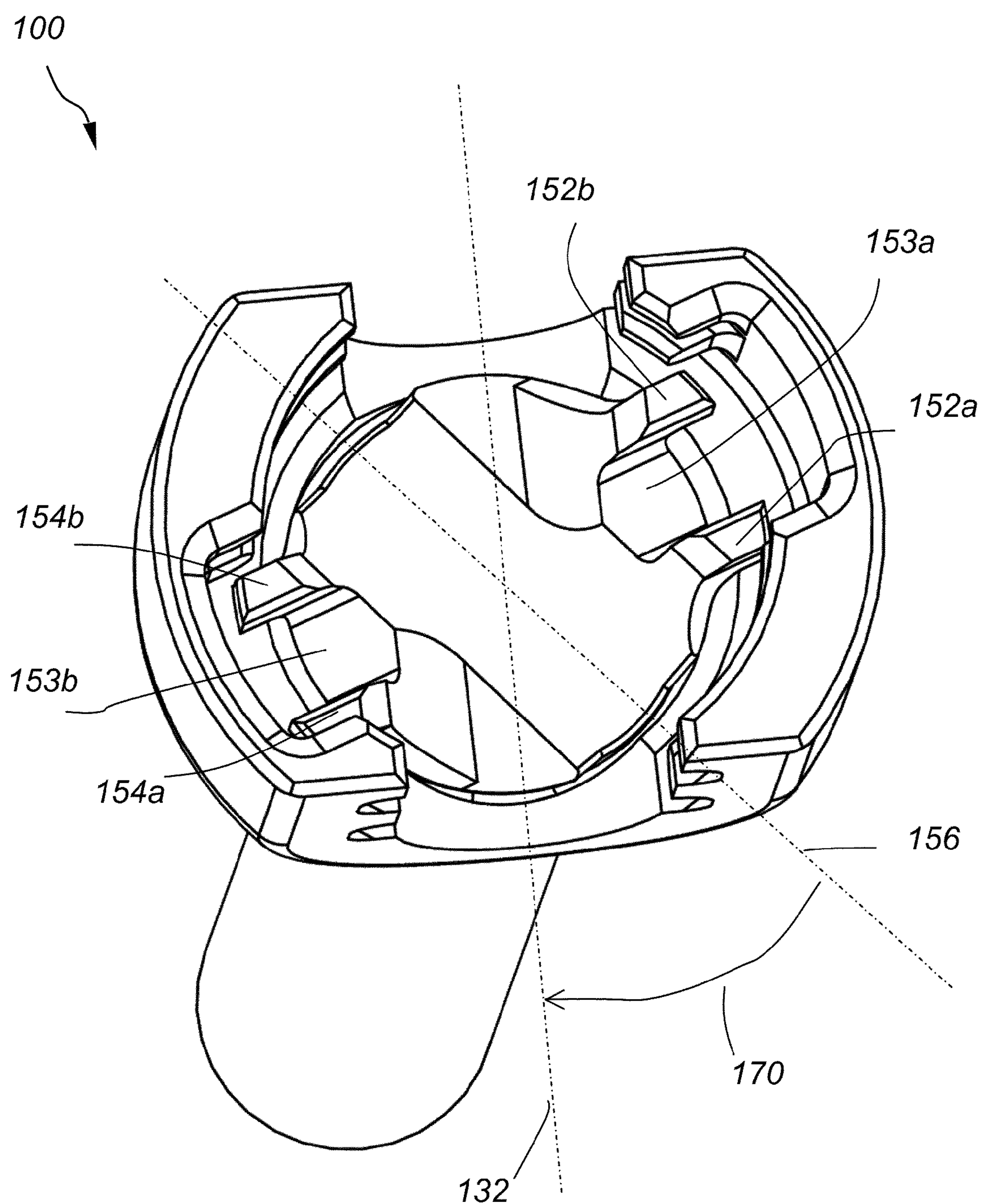
FIG. 9 is a top perspective view of the head with the installed washer.
Figure 13:
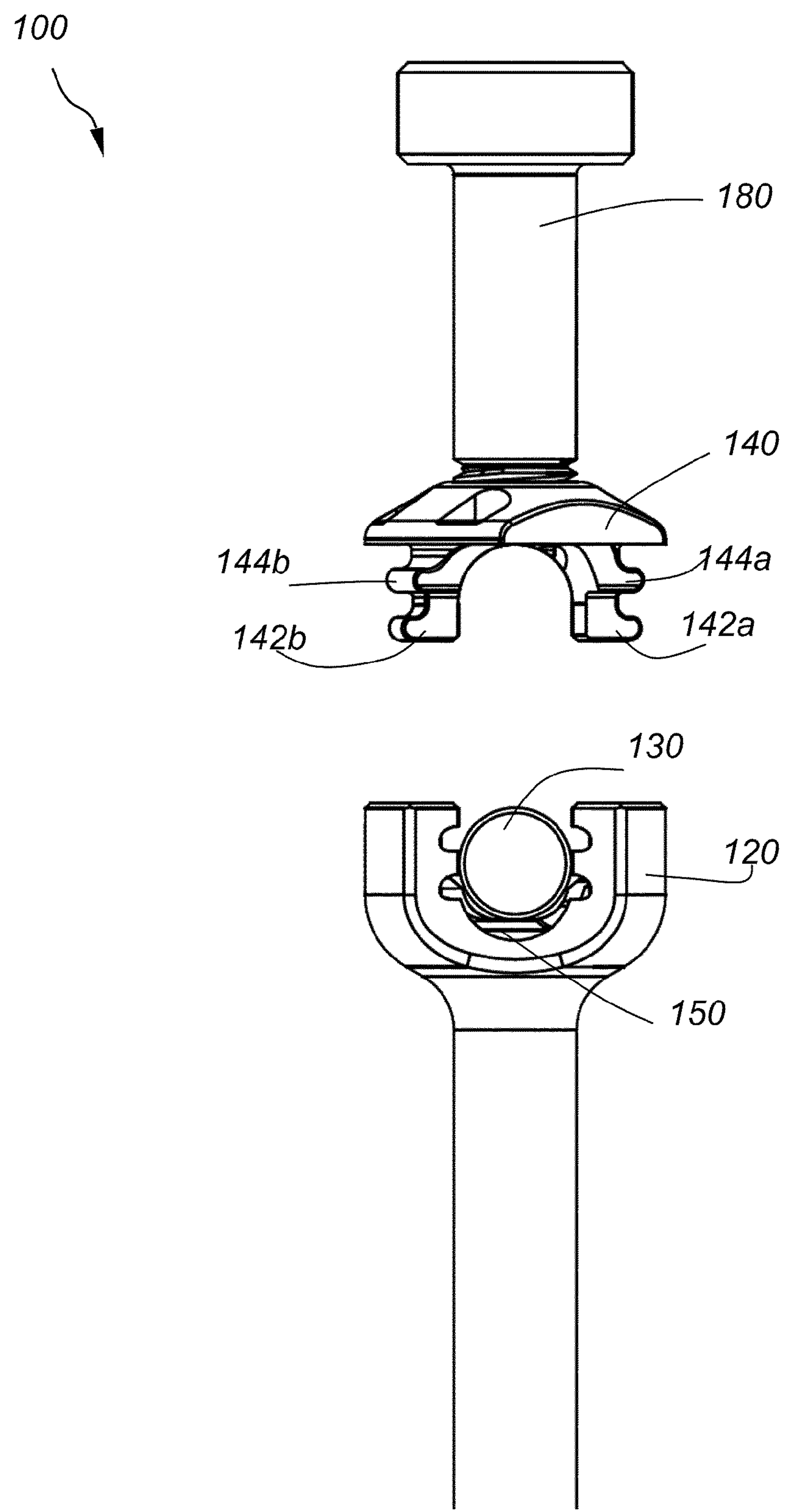
FIG. 13 is a side view of the head with the installed washer and stabilization rod and a side view of the cap before installation.
Figure 14:
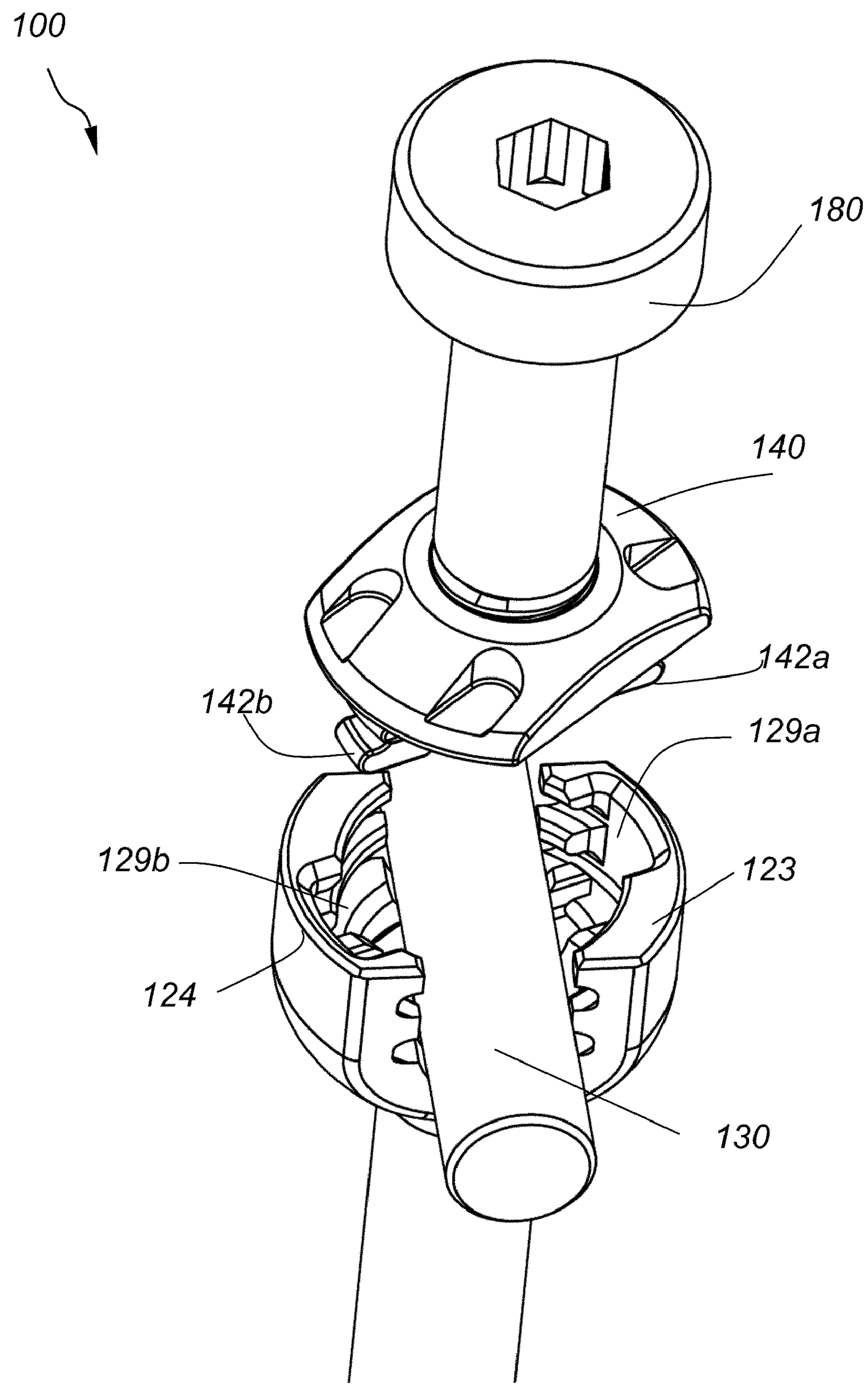
FIG. 14 is a top view of the head with the installed washer and stabilization rod and a top view of the cap before installation.
Figure 24:
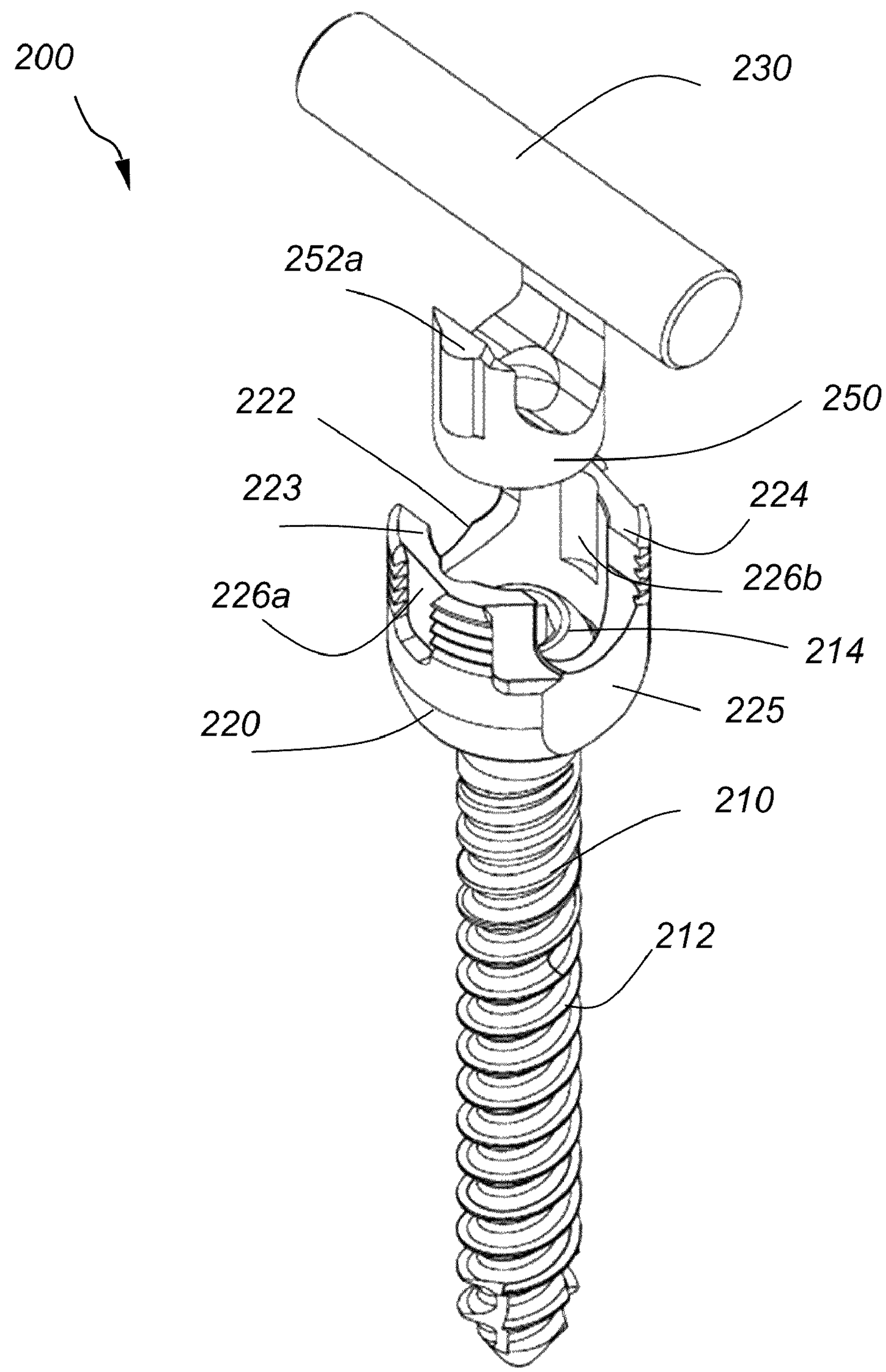
FIG. 24 is an exploded perspective view of another embodiment of the spinal screw assembly.
Figure 31:
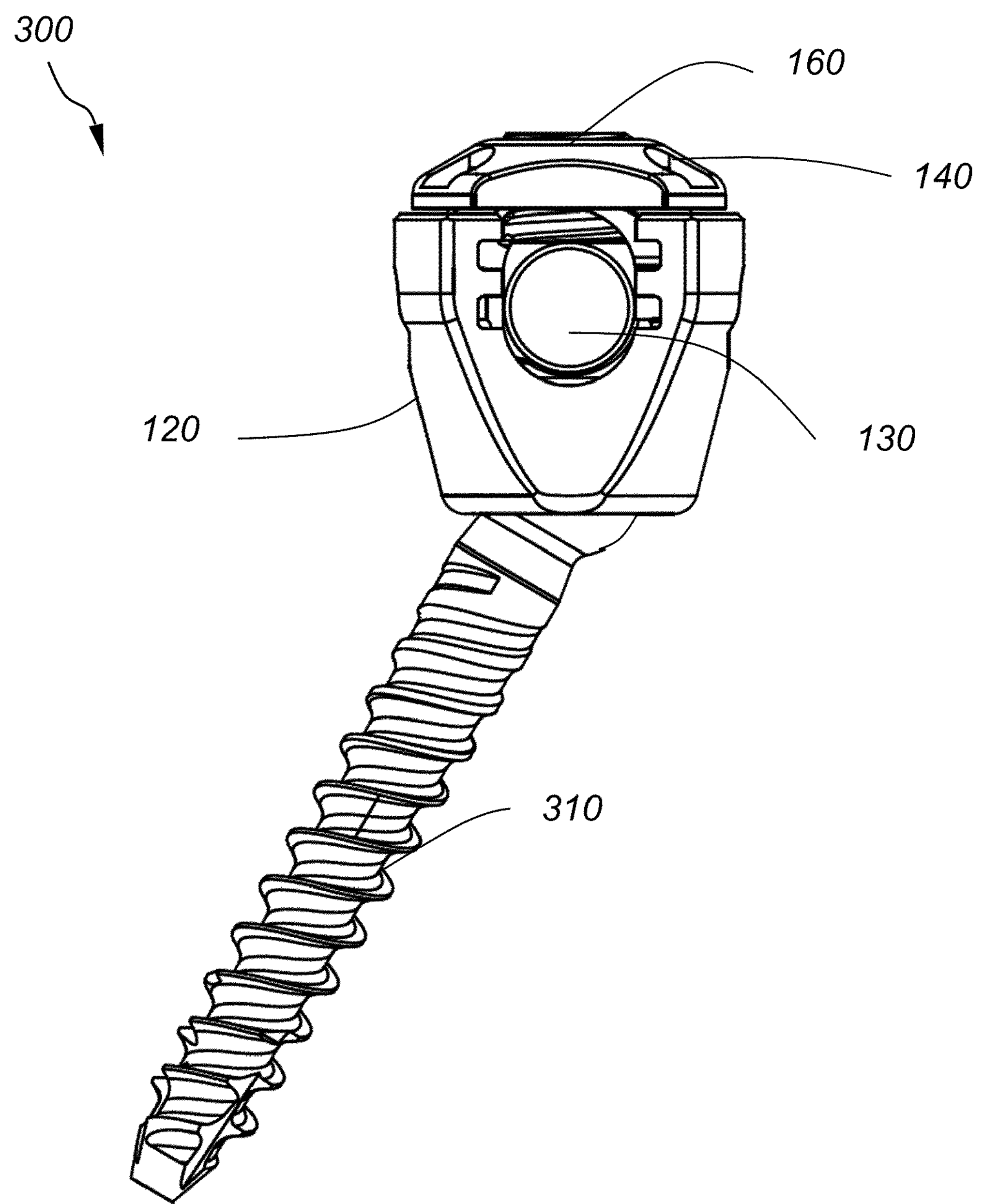
FIG. 31 is another embodiment of the spinal screw assembly for a polyaxial screw.

Referring to FIG. 2, FIG. 3 and FIG. 4, a spinal screw assembly 100 includes an anchoring portion 110, a tulip-shaped head 120, a washer 150, a stabilization rod 130, a cap 140 and a locking element 160. The anchoring portion 110 is usually a screw having outer threads, as shown in FIG. 24. In other embodiments, anchoring portion 110 is a pin (shown in FIG. 2) or a hook (not shown). The head 120 includes a U-shaped slot 122 (shown in FIG. 5) dimensioned to receive the stabilization rod 130. The U-shaped slot is formed by two legs 123, 124 extending from a base 125. Base 125 includes a groove 126 dimensioned to receive the washer 150, shown in FIG. 6. Referring to FIG. 7, and FIG. 8, washer 150 is a circular ring-shaped plate having a first set of wings 152*a*, 152*b* and a second set of wings 154*a*, 154*b*, extending from opposite edges of the top surface 151*a*. Wings 152*a*, 152*b* are dimensioned to engage a groove 127*a* formed in the inner lower portion of leg 123. Wings 154*a*, 154*b* are dimensioned to engage a grove 128*a* formed in the inner lower portion of leg 124. Wings 152*a*, 152*b* are separated by a slot 153*a* and wings 154*a*, 154*b* are separated by a slot 153*b*. Slots 153*a*, 153*b* are dimensioned to receive lower protrusions 142*a*, 142*b*, respectively, extending from the lower surface of cap 140, shown in FIG. 4. The top surface 151*a* of washer 150 also includes a groove 155 dimensioned to accommodate the stabilization rod 130 when the assembly is locked so that the groove axis 156 aligns parallel with the stabilization rod axis 132, as shown in FIG. 9. Cap 140 also includes upper protrusions 144*a*, 144*b* extending from the lower surface of cap 140 and formed above the lower protrusions 142*a*, 142*b*, respectively, as shown in FIG. 13. Upper protrusions 144*a*, 144*b* are dimensioned to engage grooves 127*b*, 128*b* formed in the inner upper portion of legs 123, 124, respectively. Cap 140 further includes a central bore 145 dimensioned to receive the locking element 160, which in this case is a threaded screw configured to engage inner threads in the bore 145, shown in FIG. 4. The anchoring portion 110 is shown in the embodiment of FIG. 2 to be integral with the head 120. In other embodiments the anchoring portion 110 is a separate component from the head 120 and the two are joined together via a threading mechanism or a snap-in mechanism, as shown in the embodiments of FIG. 24 and FIG. 31.

Figure 10:
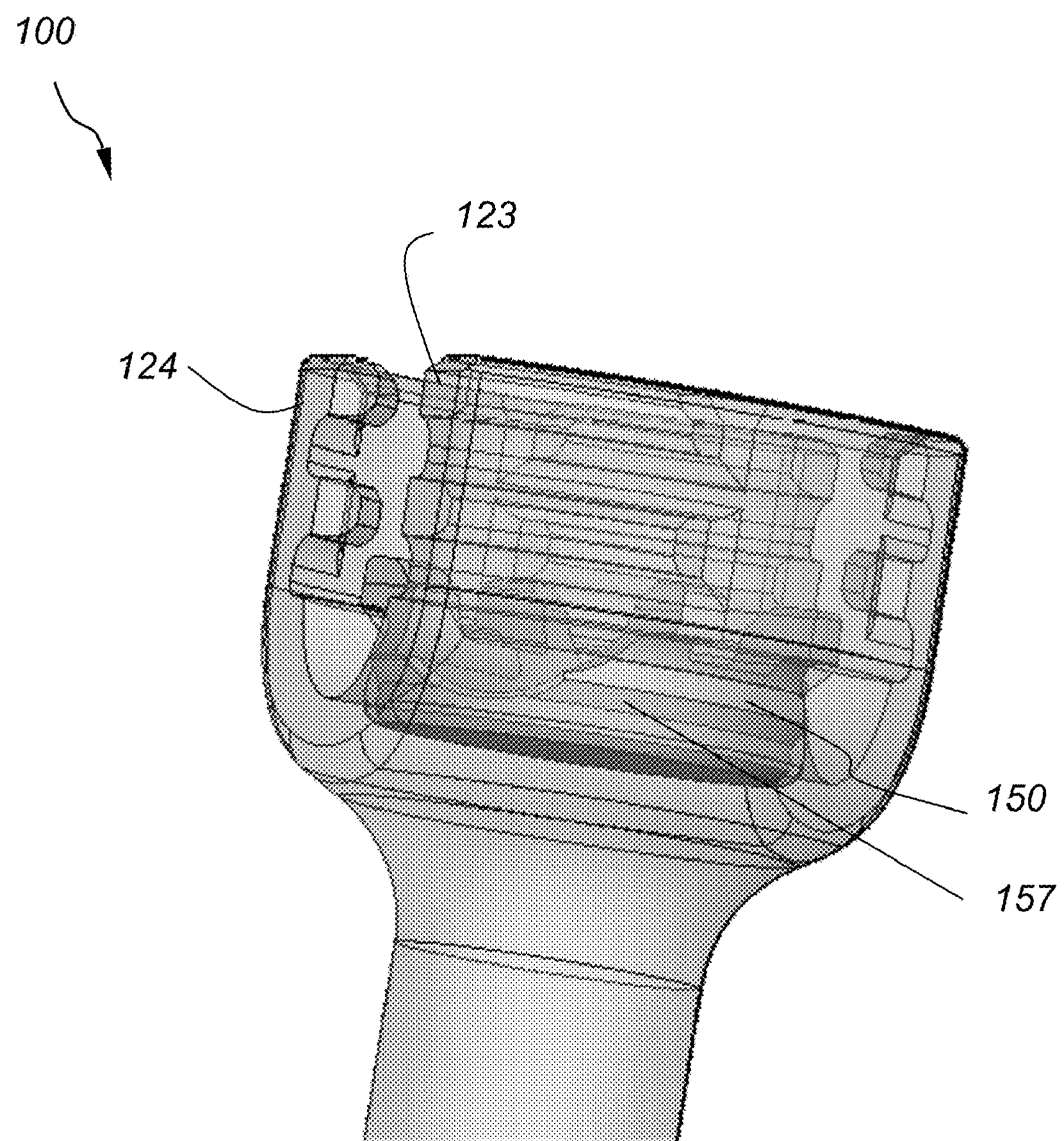
FIG. 10 is a side transparent view of the head with the installed washer.
Figure 11:
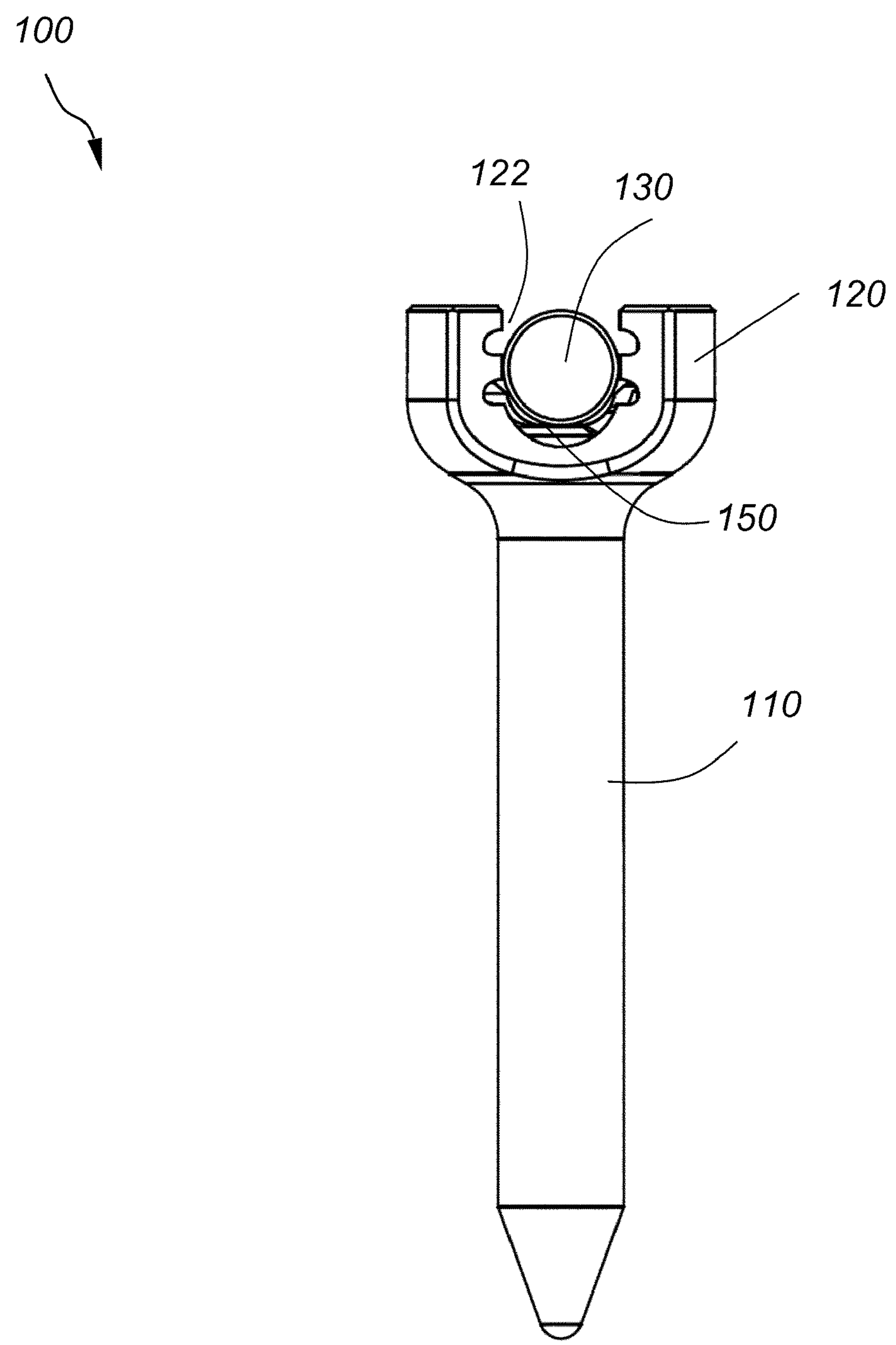
FIG. 11 is a side view of the head with the installed washer and stabilization rod.
Figure 12:
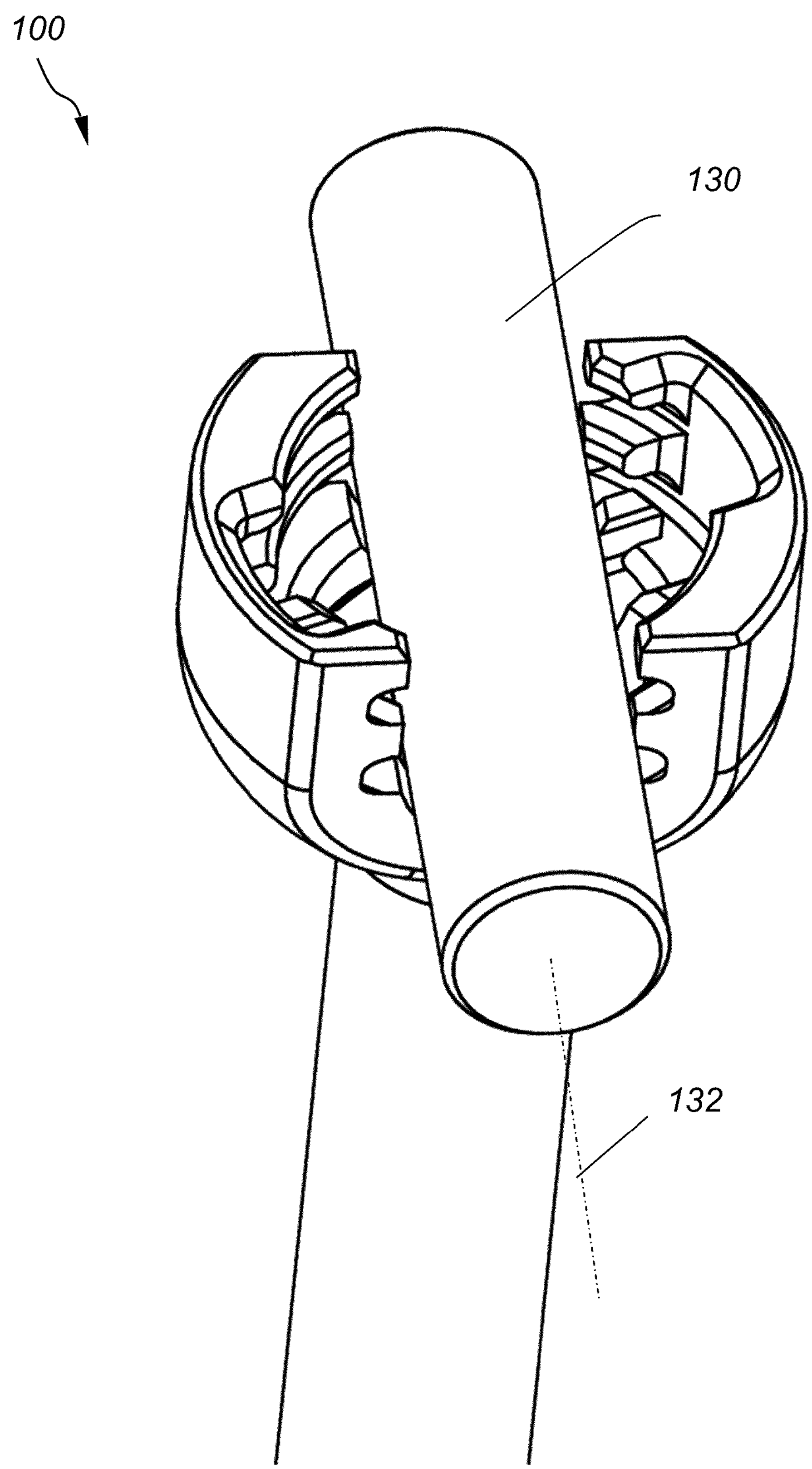
FIG. 12 is a top view of the head with the installed washer and stabilization rod.
Figure 15:
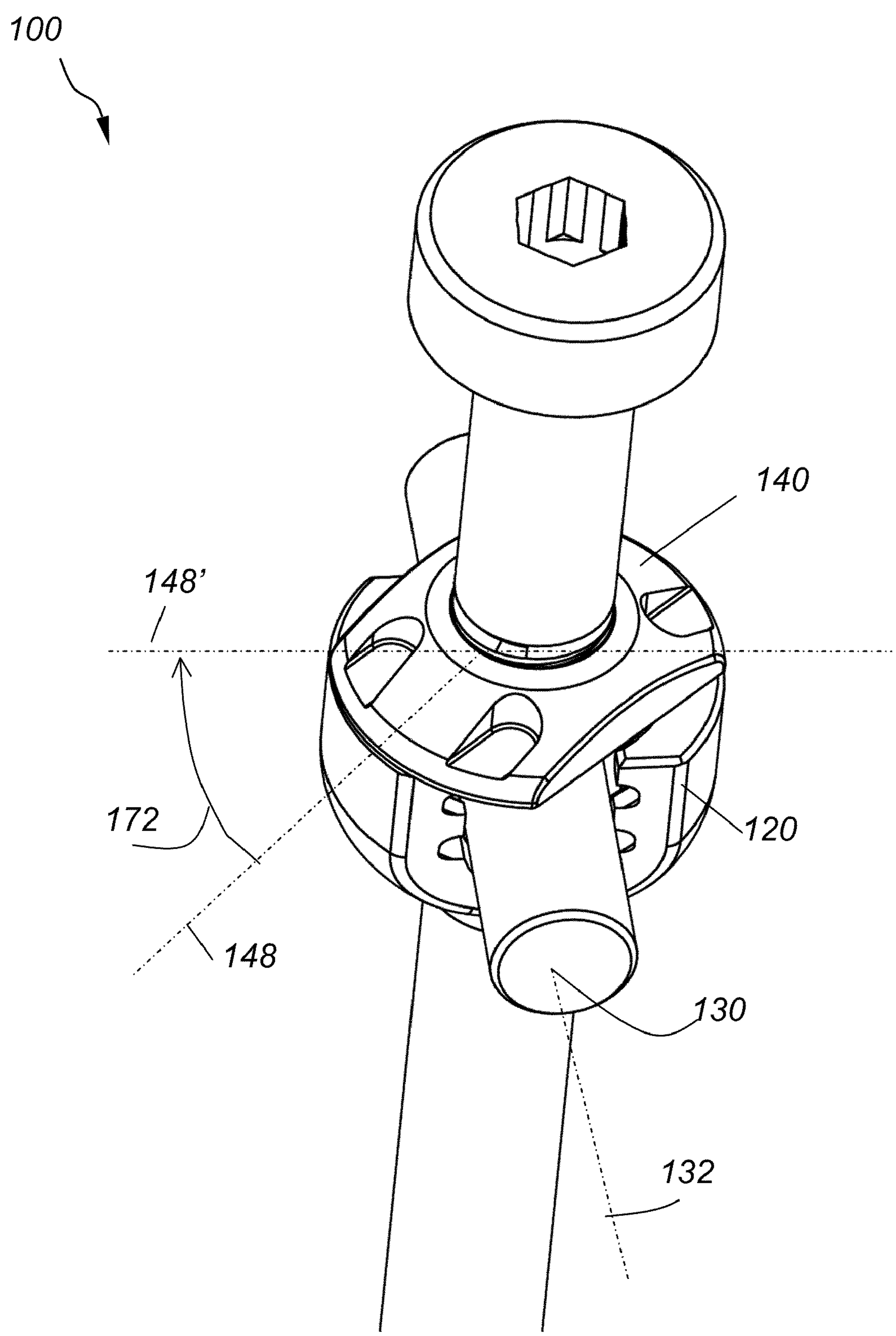
FIG. 15 is a top view of the head with the installed washer and stabilization rod and the cap inserted in the head.
Figure 16:
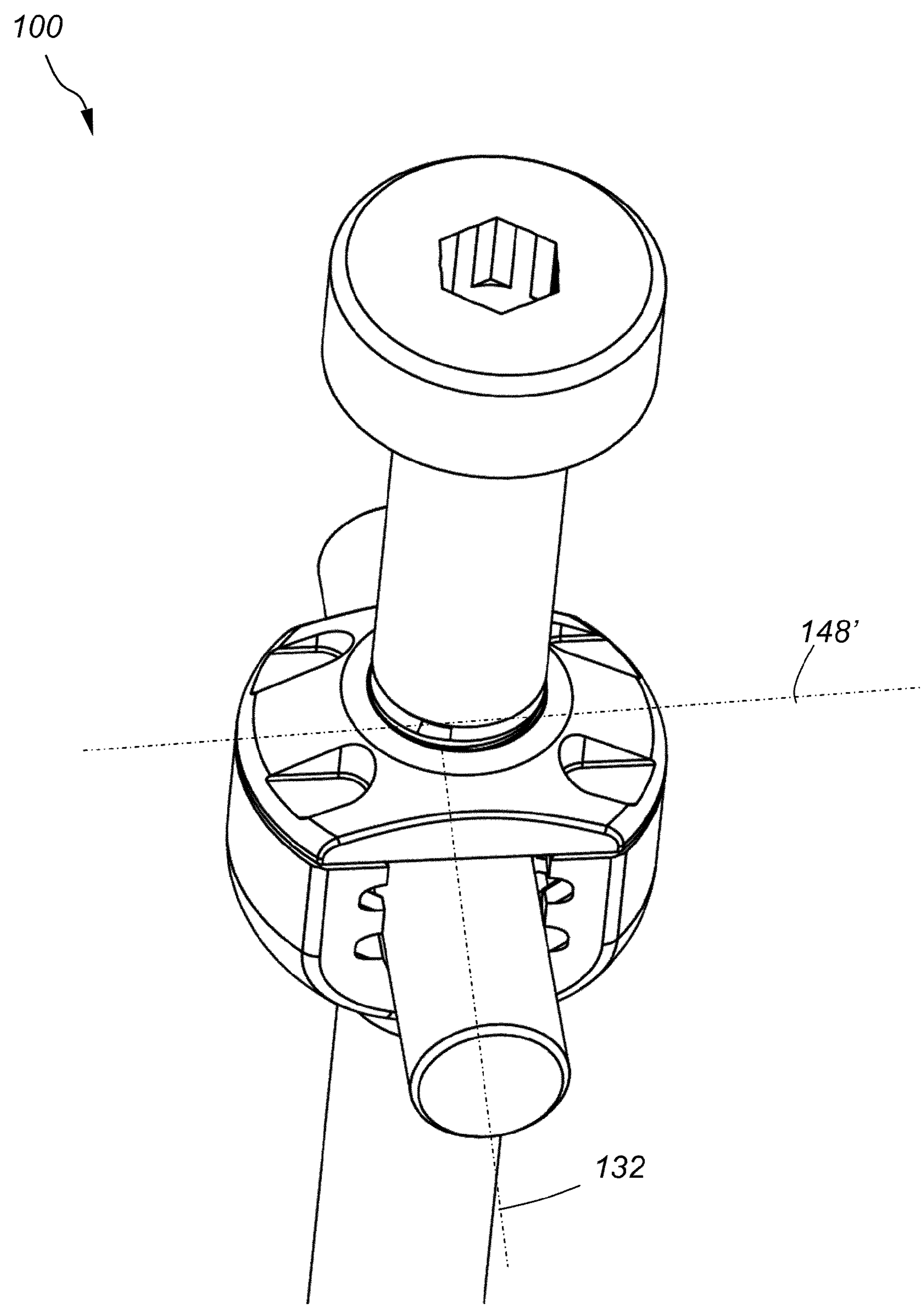
FIG. 16 is a top view of the head with the installed washer and stabilization rod and the cap inserted in the head and rotated by a quarter turn.
Figure 17:
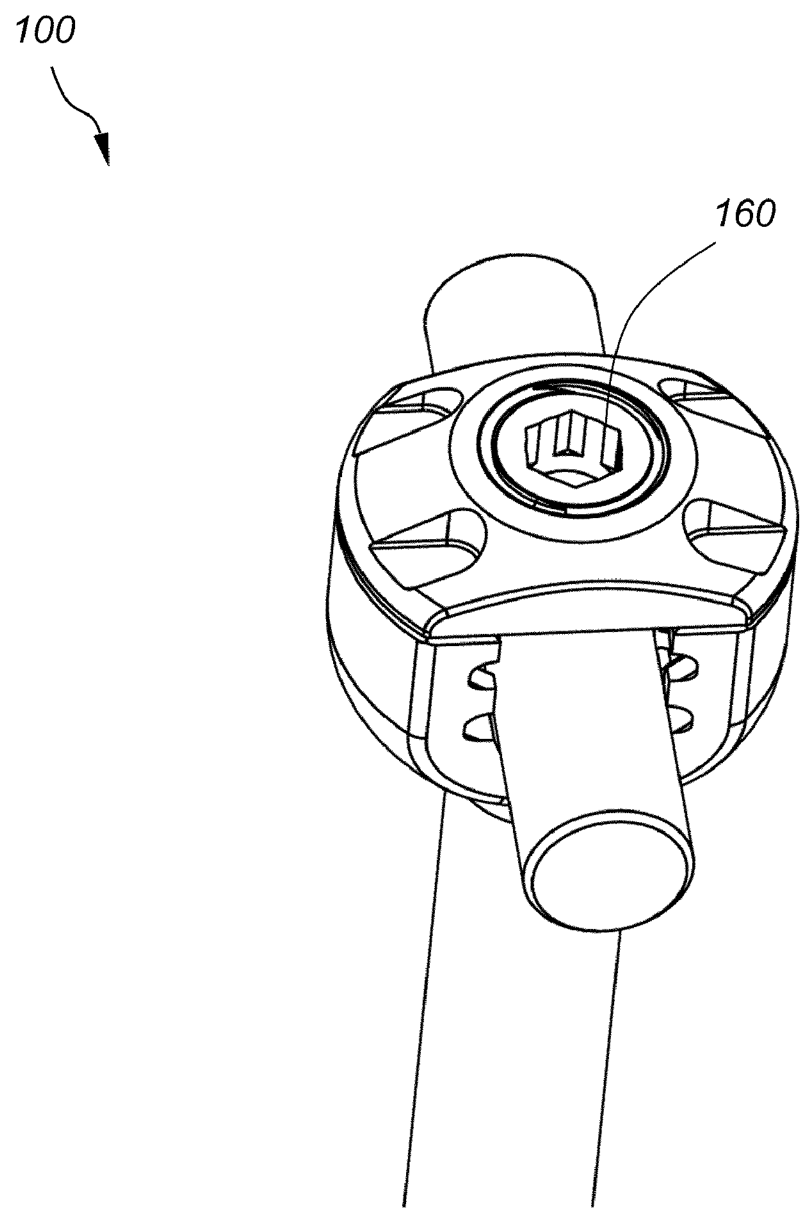
FIG. 17 is a top view of the head with the installed washer, stabilization rod, cap and locking element.
Figure 18:
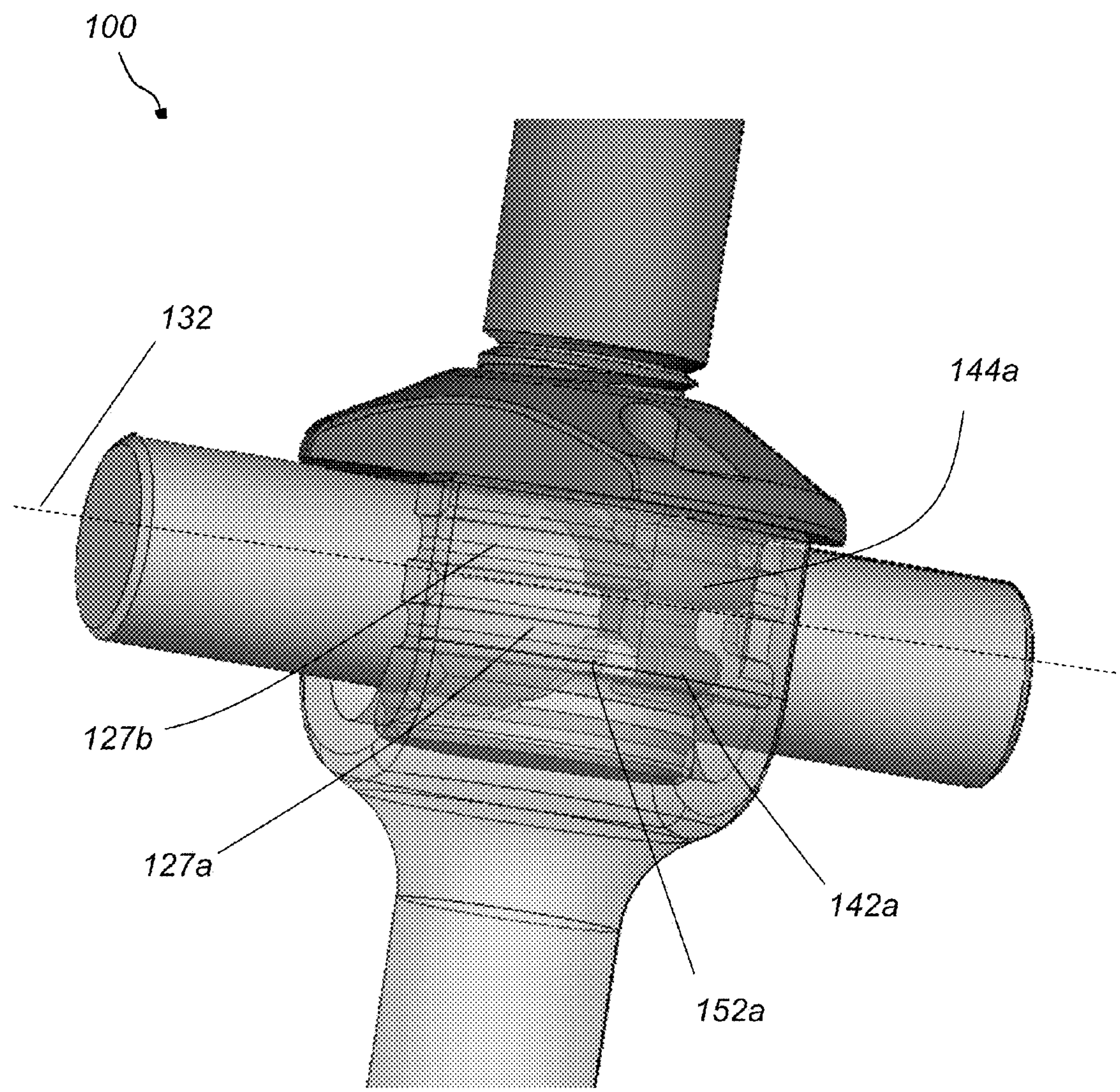
FIG. 18 is a side transparent view of the assembly of FIG. 15.
Figure 19:
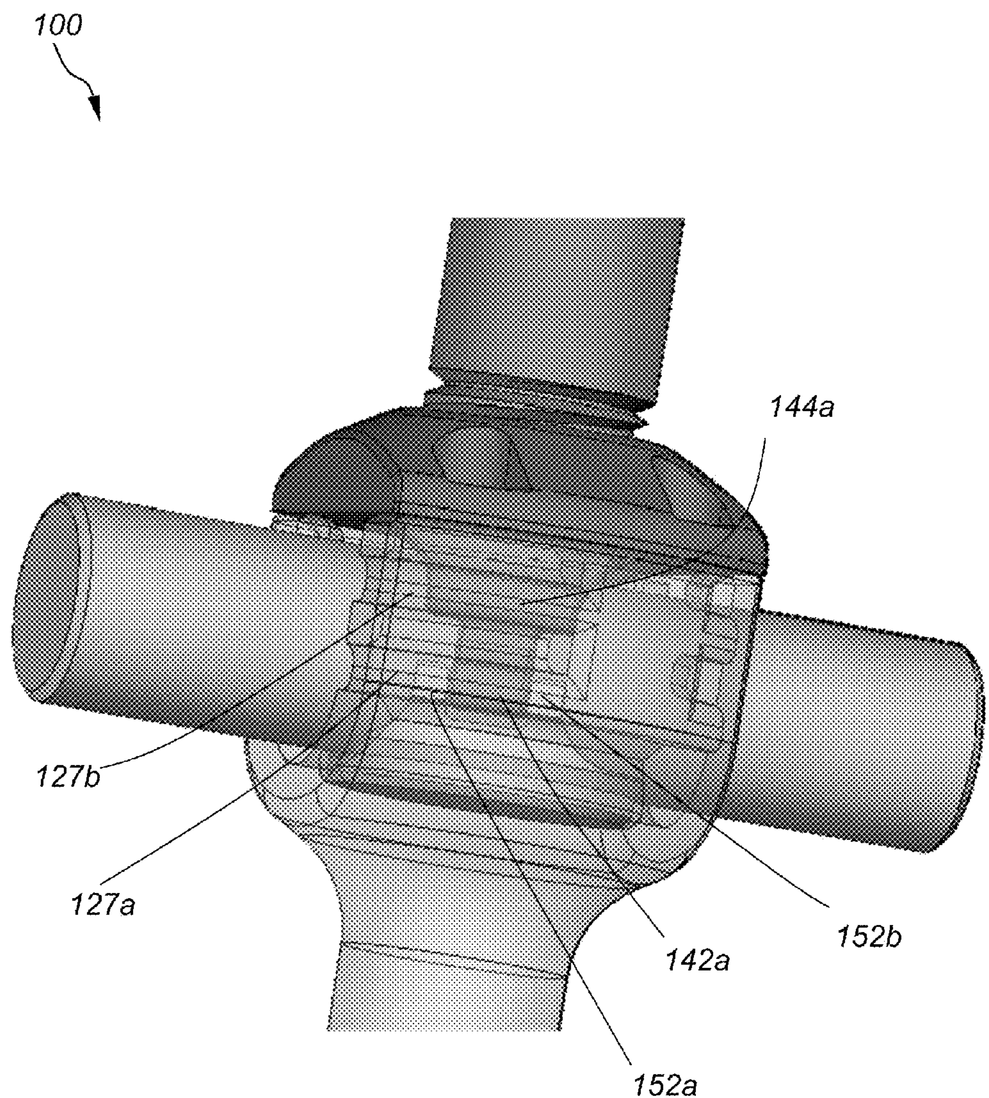
FIG. 19 is a side transparent view of the assembly of FIG. 16.
Figure 20:
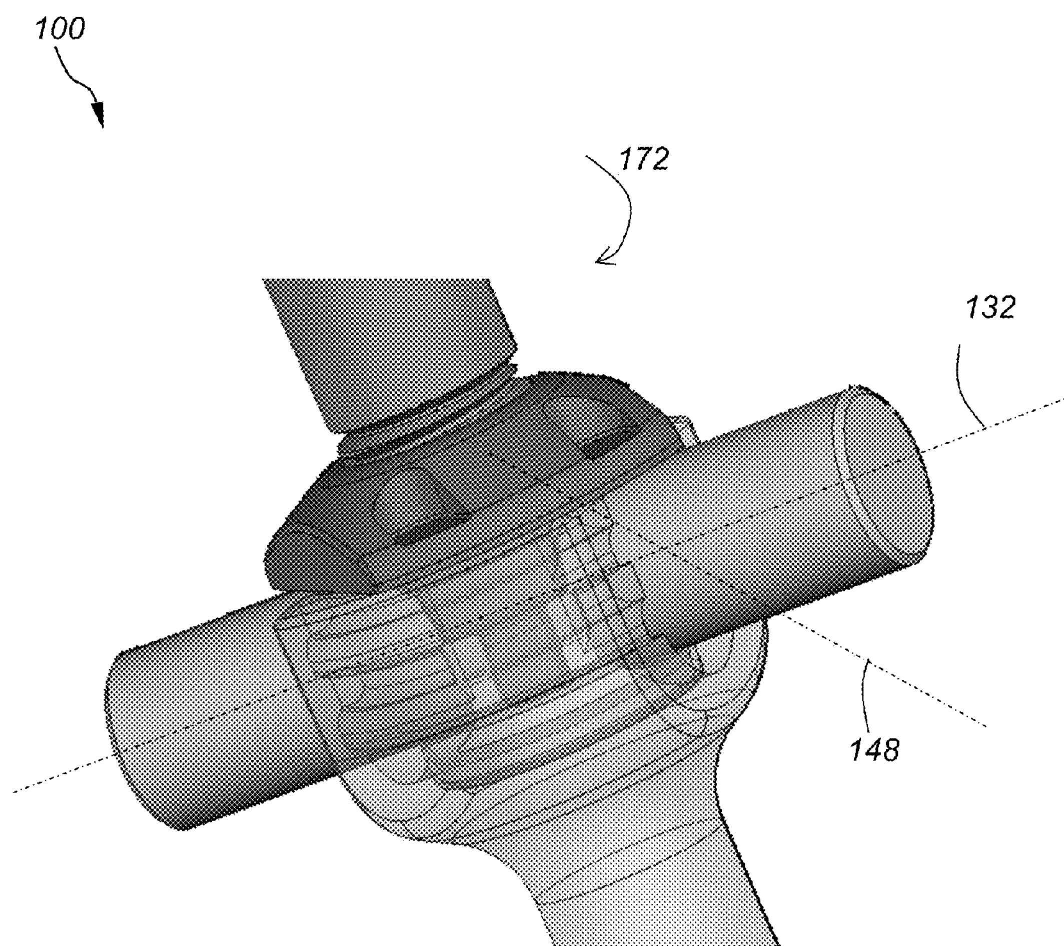
FIG. 20 is another side transparent view of the assembly of FIG. 15.
Figure 21:
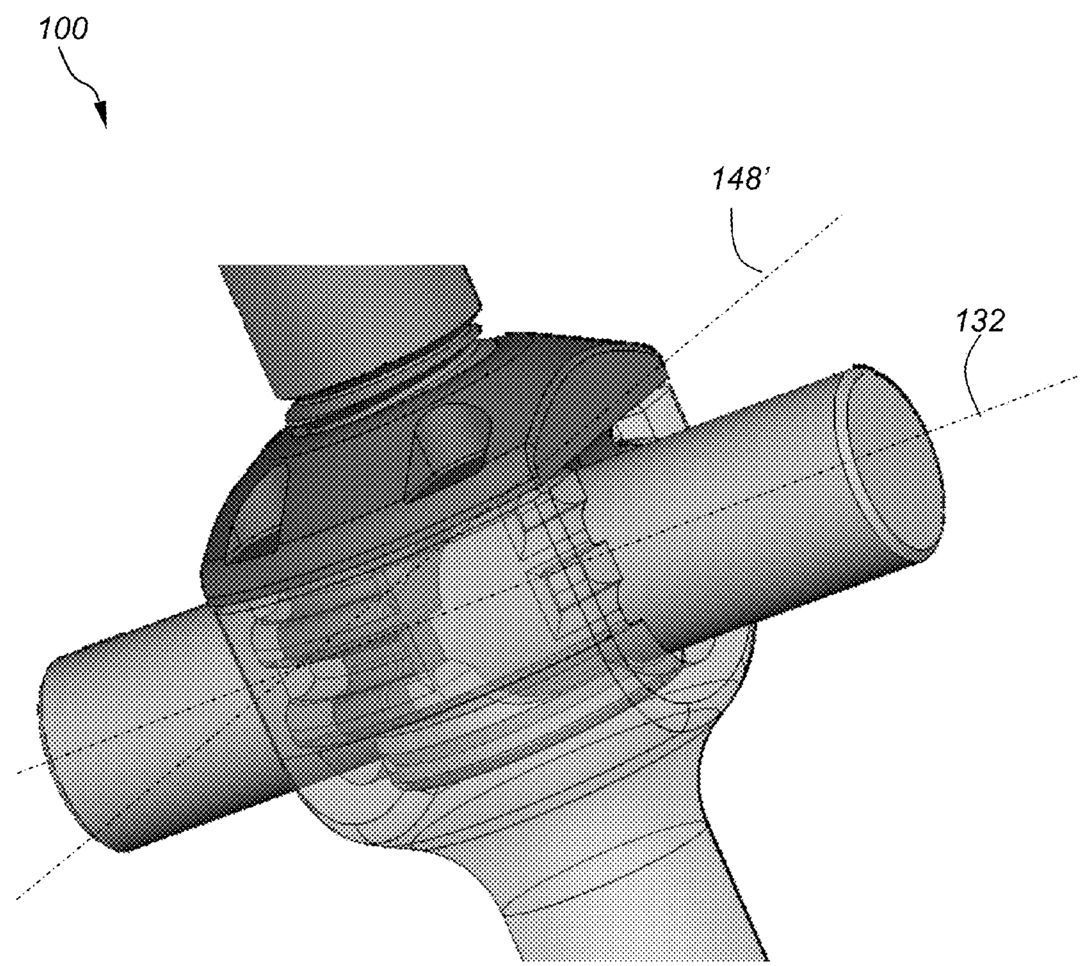
FIG. 21 is another side transparent view of the assembly of FIG. 16.
Figure 22:
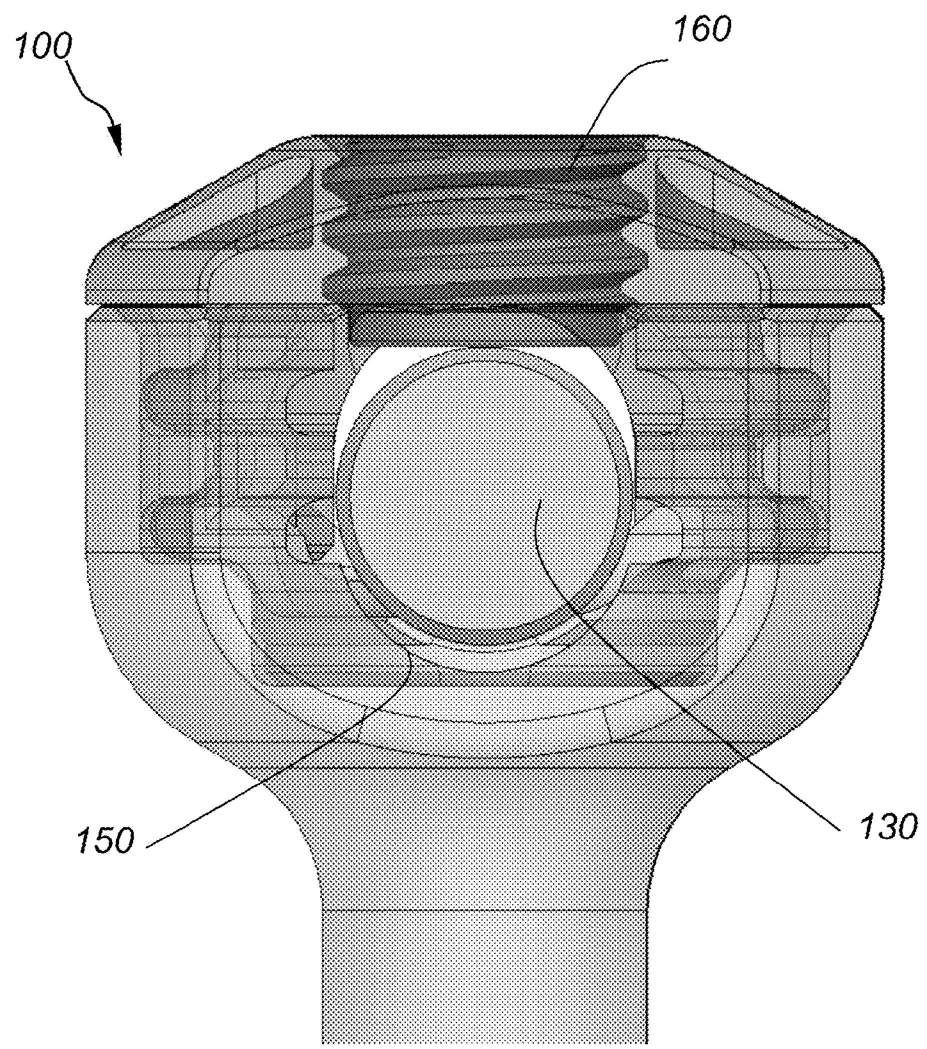
FIG. 22 is a side transparent view of the head with the installed washer, stabilization rod, cap and locking element.
Figure 23:
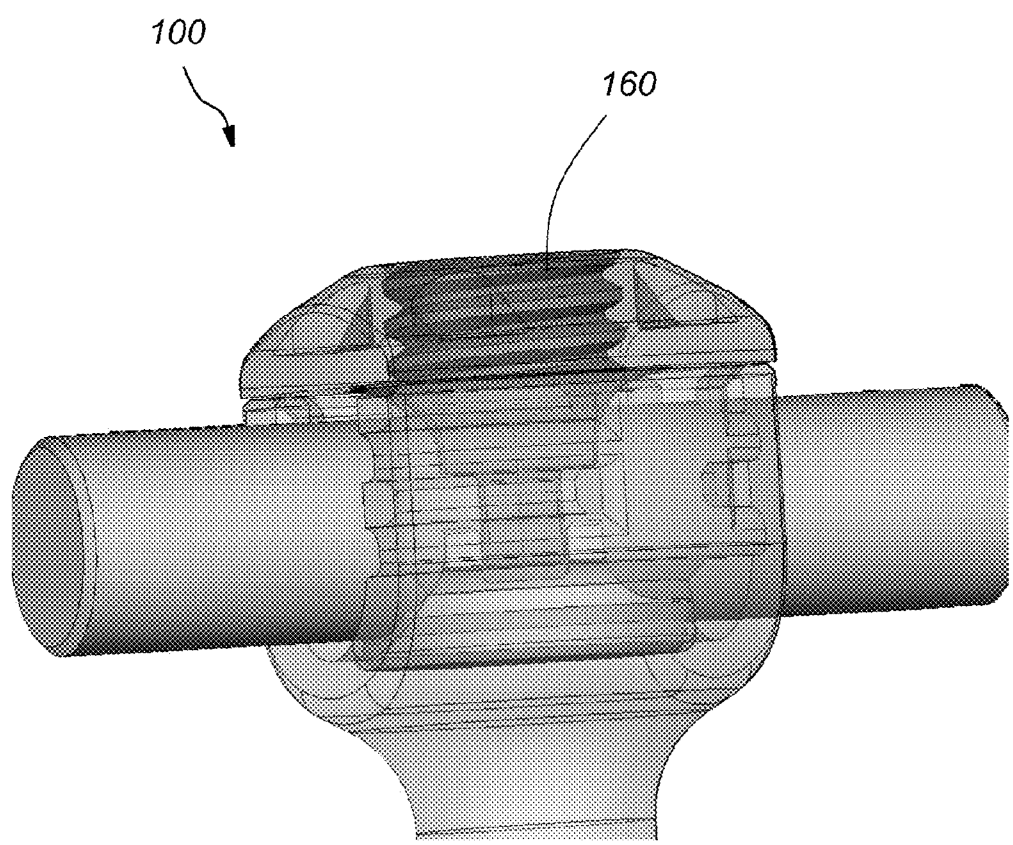
FIG. 23 is another side view of the head with the installed washer, stabilization rod, cap and locking element.

In operation the anchoring portion 110 is implanted into a spinal location and the washer 150 is threaded into base 125, so that the bottom edge 157 engages the groove 126 and the wings 152*a*, 152*b* and 154*a*, 154*b* engage the lower grooves 127*a*, 128*a* of the legs 123, 124, respectively, as shown in FIG. 9 and FIG. 10. Next the stabilization rod 130 is placed in the slot 122, as shown in FIG. 11, FIG. 12, and then the cap 140 is inserted in the head 120 so that the lower protrusions 142*a*, 142*b* engage the spaces 153*a*, 153*b* between the washer protrusions 152*a*, 152*b* and 154*a*, 154*b*, respectively, while the upper protrusions 144*a*, 144*b* engage the upper grooves 127*b*, 128*b* of the legs 123, 124, respectively, as shown in FIG. 15, FIG. 18 and FIG. 20. Next, the cap 140 with the engaged washer 150 are rotated together in the direction of arrow 172 by a small segment to lock the position of the cap and to align the axis 148 of the cap perpendicular to the rod axis 132, as shown in FIG. 15, FIG. 16, FIG. 19 and FIG. 21. This cap and washer rotation also aligns the axis 156 of the washer groove 155 parallel with the stabilization rod axis 132, as was mentioned above. In one example, the cap 140 and the washer 150 are rotated by a quarter turn. Finally, the locking element 160 is threaded into the bore 145 to tighten the position of the stabilization rod 130 down onto the washer 150, as shown in FIG. 17, FIG. 22 and FIG. 23.

Referring to FIG. 24-FIG. 30, another embodiment of the spinal screw assembly 200 includes an anchoring portion 210, a tulip-shaped head 220, a washer 250, a stabilization rod 230, a cap 240 and a locking element 260. The anchoring portion 210 is a screw having outer threads 212. The head 220 includes a U-shaped slot 222 dimensioned to receive the stabilization rod 130. The U-shaped slot is formed by two legs 223, 224 extending from a base 225. Legs 223, 224 include slots 226*a*, 226*b*, respectively, dimensioned to receive protrusions 252*a*, 252*b*, respectively of the washer 250, shown in FIG. 25. In this embodiment, screw 210 is not integral with the base 220 and includes a spherical head 214 dimensioned to sit in the base 225 while the threaded portion of the screw passes through a bore formed in the base 225 of the head 220. This embodiment provides for multiaxial orientation of the screw 220 relative to the stabilization rod 230. Cap 240 includes two legs 242, 244, extending from the edges of the lower surface 241*b*. The inner surfaces of legs 242, 244 include threads 243 dimensioned to engage outer threads 221 formed in the outer surfaces of legs 223, 224 of head 220.

Figure 25:
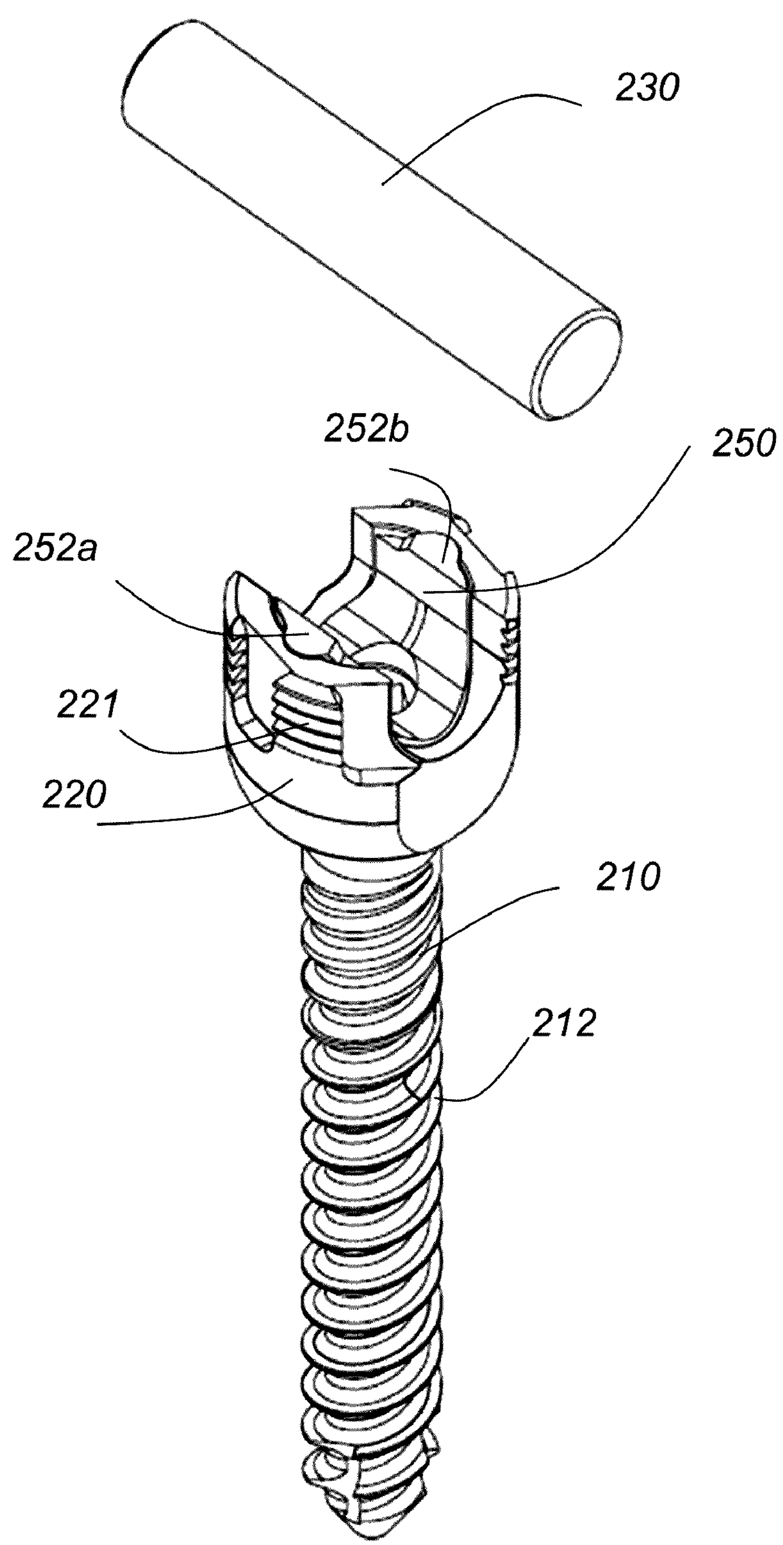
FIG. 25 is a top perspective view of the spinal screw assembly of FIG. 24 depicting the head with the installed washer.
Figure 26:
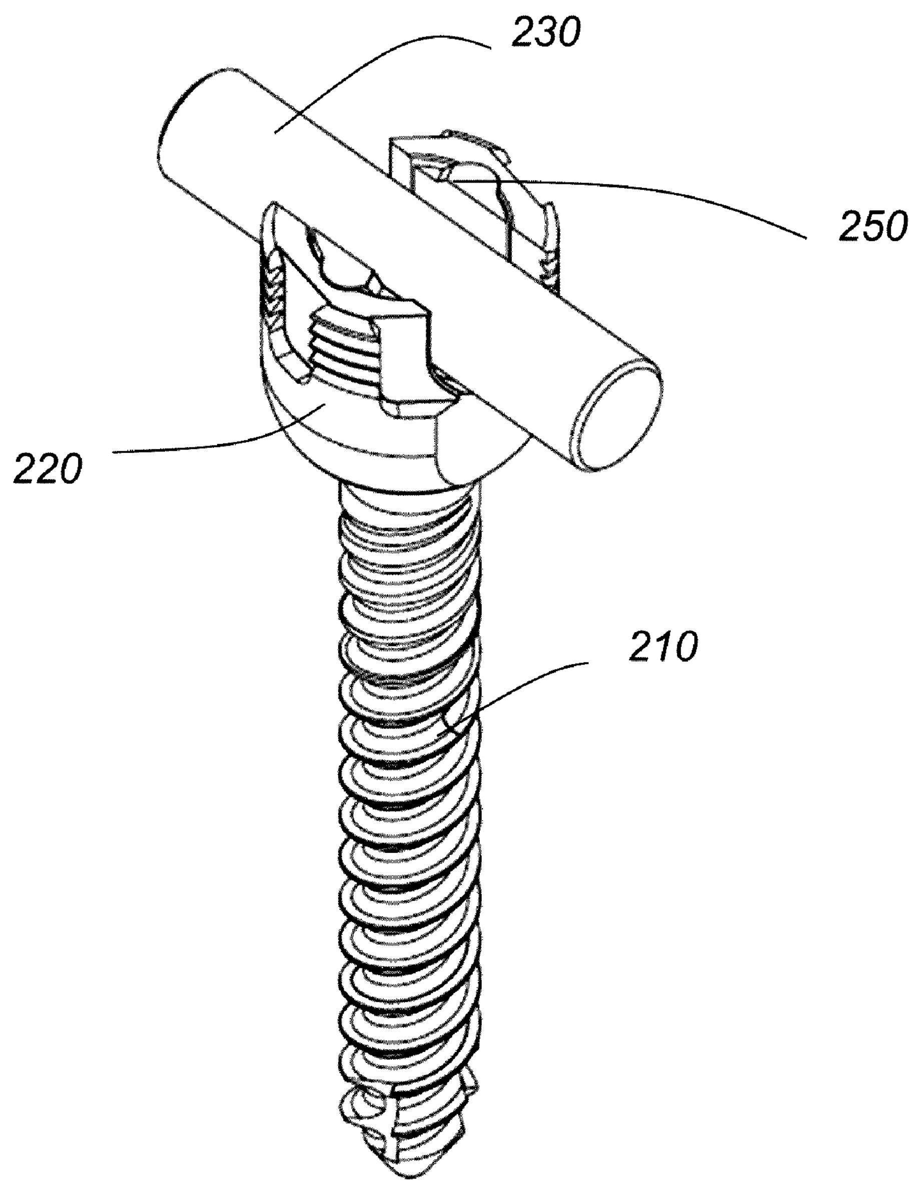
FIG. 26 is a top perspective view of the spinal screw assembly of FIG. 24 depicting the head with the installed washer and rod.
Figure 27:
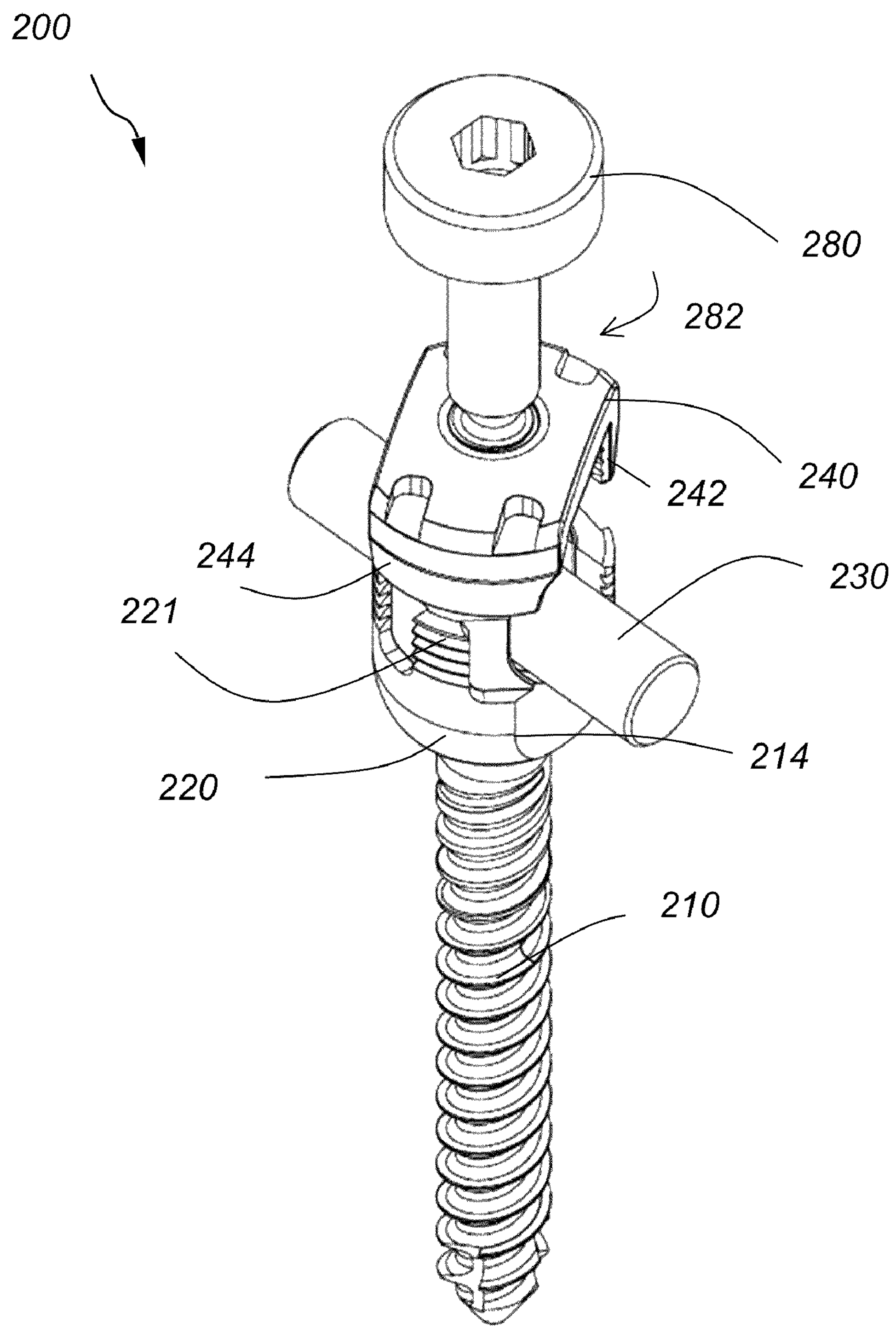
FIG. 27 is a top perspective view of the spinal screw assembly of FIG. 24 depicting the head with the installed washer and rod and the cap before insertion.
Figure 28:
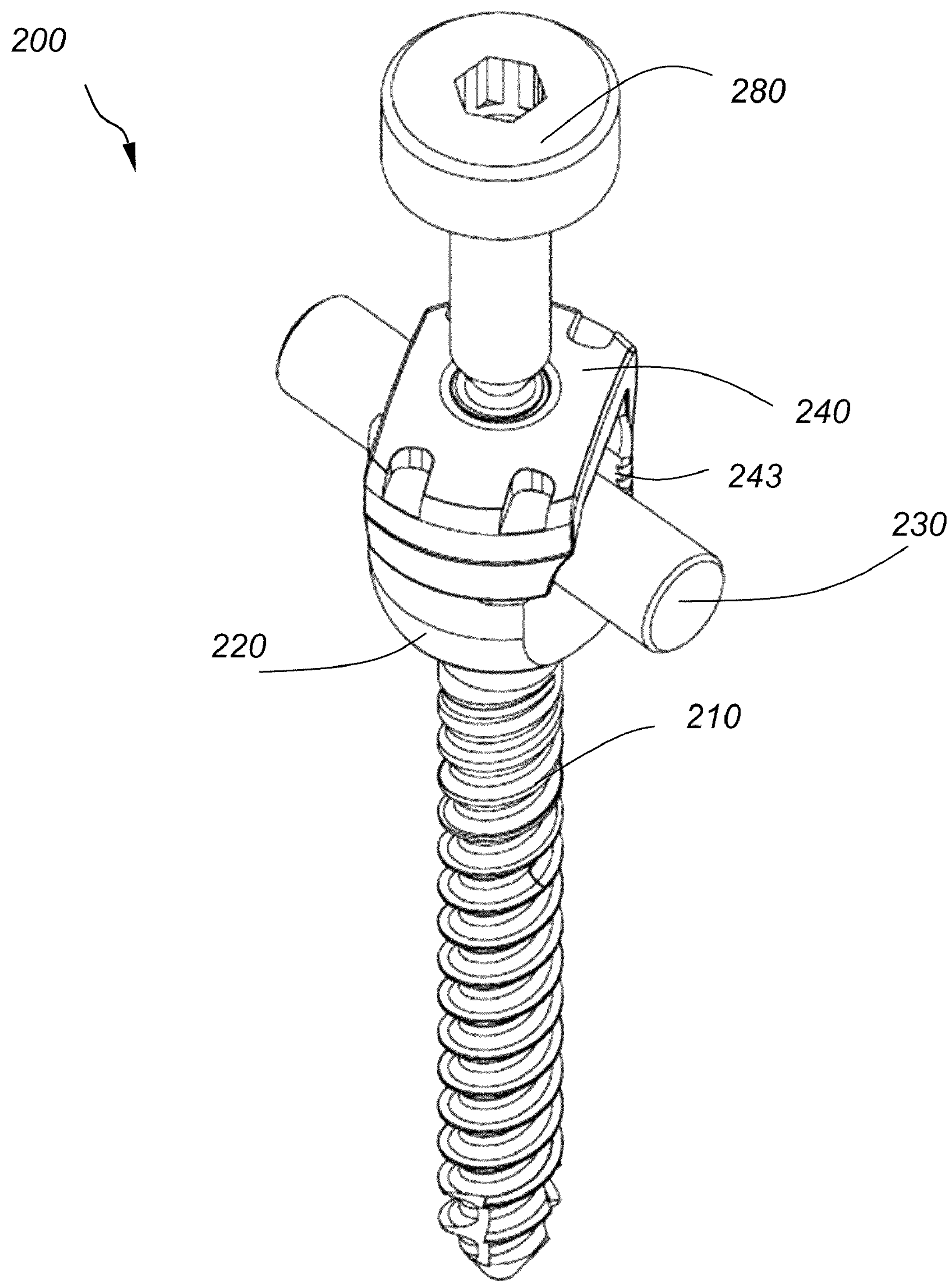
FIG. 28 is a top perspective view of the spinal screw assembly of FIG. 24 depicting the head with the installed washer, rod and the cap.
Figure 29:
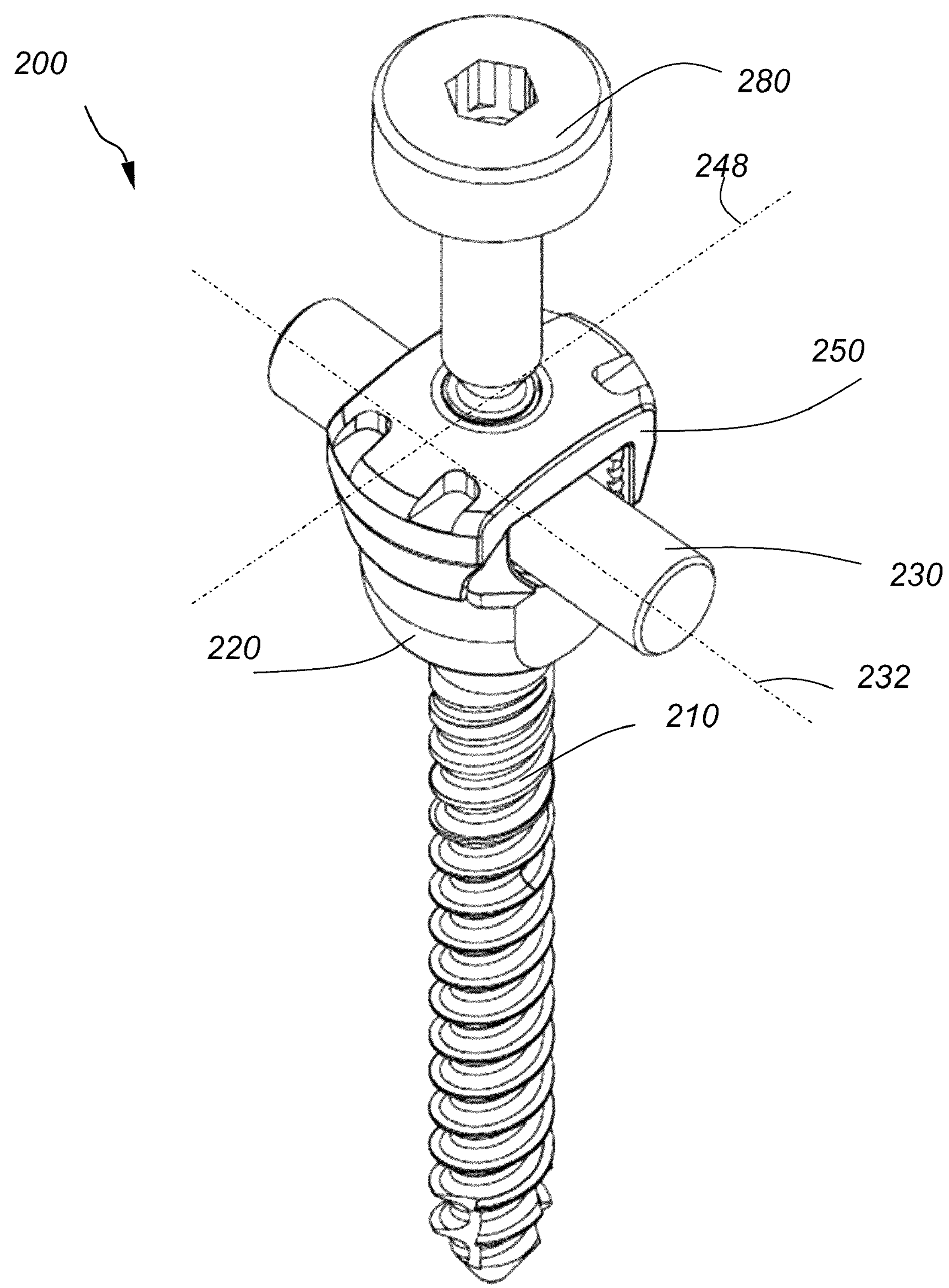
FIG. 29 is a top perspective view of the spinal screw assembly of FIG. 24 depicting the head with the installed washer, rod and the cap rotated by a quarter turn.
Figure 30:
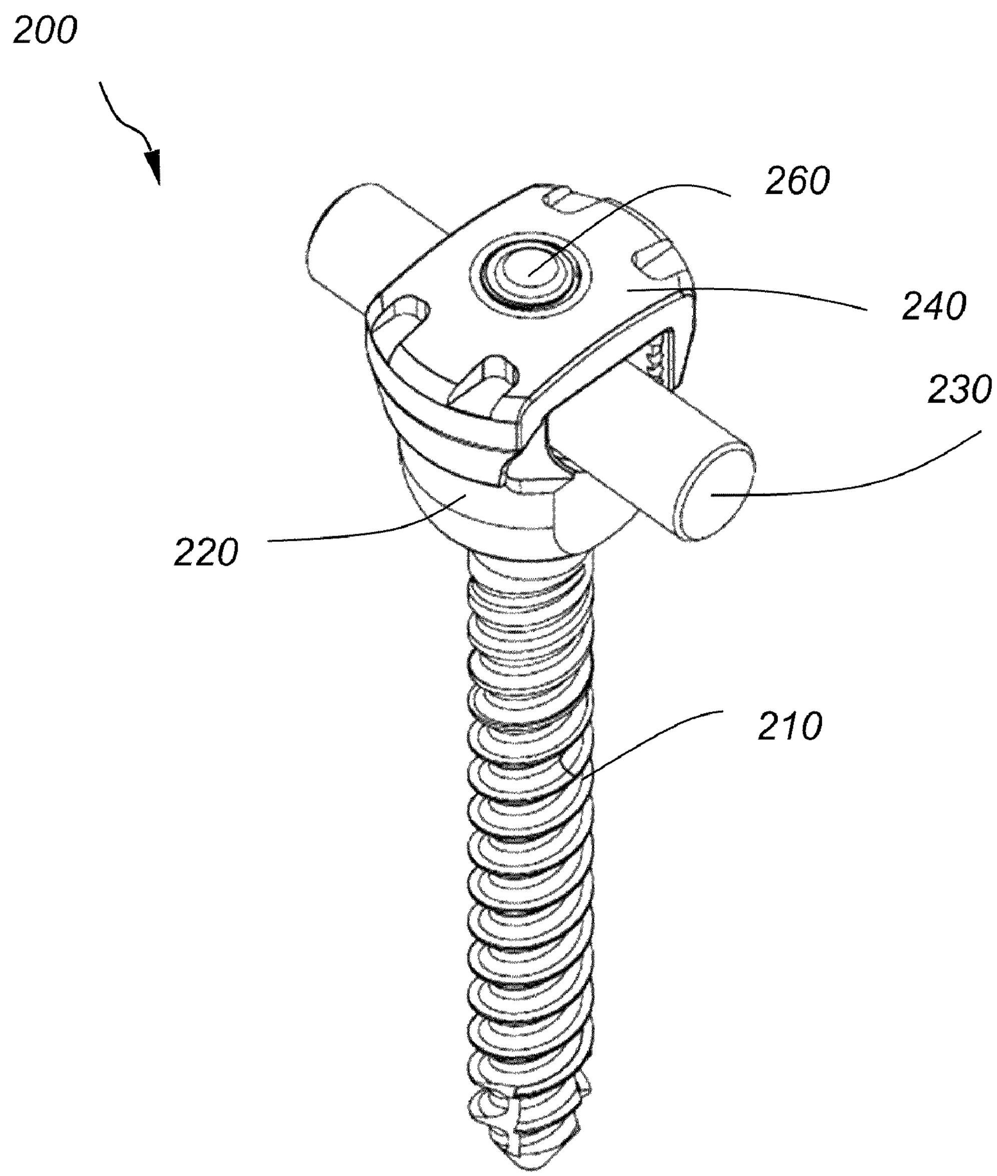
FIG. 30 is a top perspective view of the spinal screw assembly of FIG. 24 depicting the head with the installed washer, rod, cap and locking element.

In operation, screw 210 is threaded through the bore in the base 225 of head 220 and is implanted into a spinal location. Next, washer 250 is inserted into head 220, so that the side protrusions 252*a*, 252*b* engage the slots 226*a*, 226*b*, respectively, as shown in FIG. 25. Next the stabilization rod 230 is placed in the slot 222, as shown in FIG. 26, and then the cap 240 is placed on the head 220 so that the threaded legs 242, 244 engage the outer threads 221 in the head legs 223, 224, respectively, as shown in FIG. 28. Next, the cap 240 is rotated in the direction of arrow 282 by a small segment to engage side protrusions 252*a*, 252*b* of the washer 250 through the slots 226*a*, 226*b*, respectively, and thereby to lock the position of the washer 250 and the underlying spherical screw head 214. In one example, the cap 240 is rotated by a quarter turn, thereby aligning the axis 248 of the cap perpendicular to the rod axis 232, as shown in FIG. 29. Finally, the locking element 260 is threaded into the bore 245 to lock the position of the stabilization rod 230 down onto the washer 250, as shown in FIG. 30.

Figure 32:
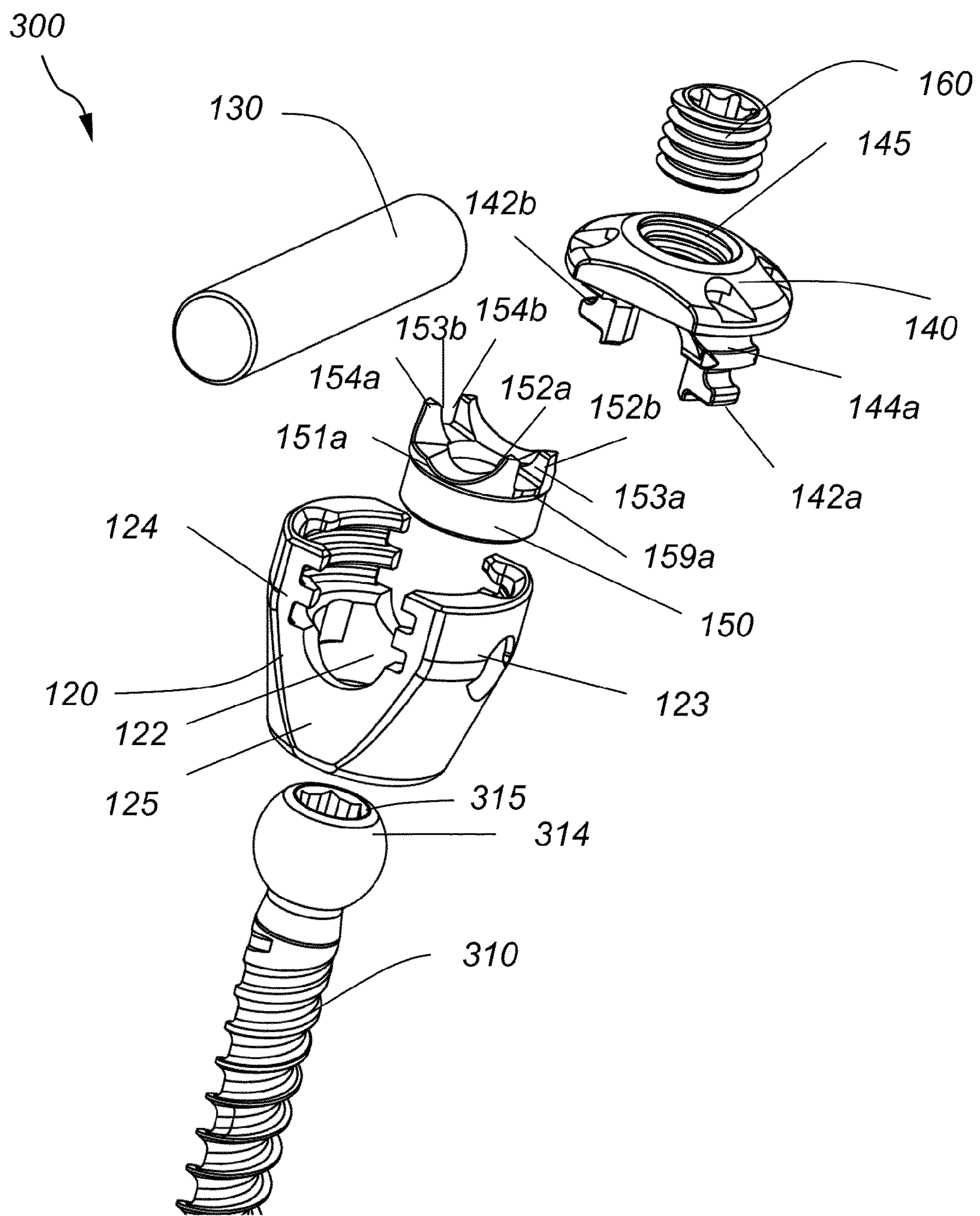
FIG. 32 is an exploded perspective view of the spinal screw assembly of FIG. 31.
Figure 33A:
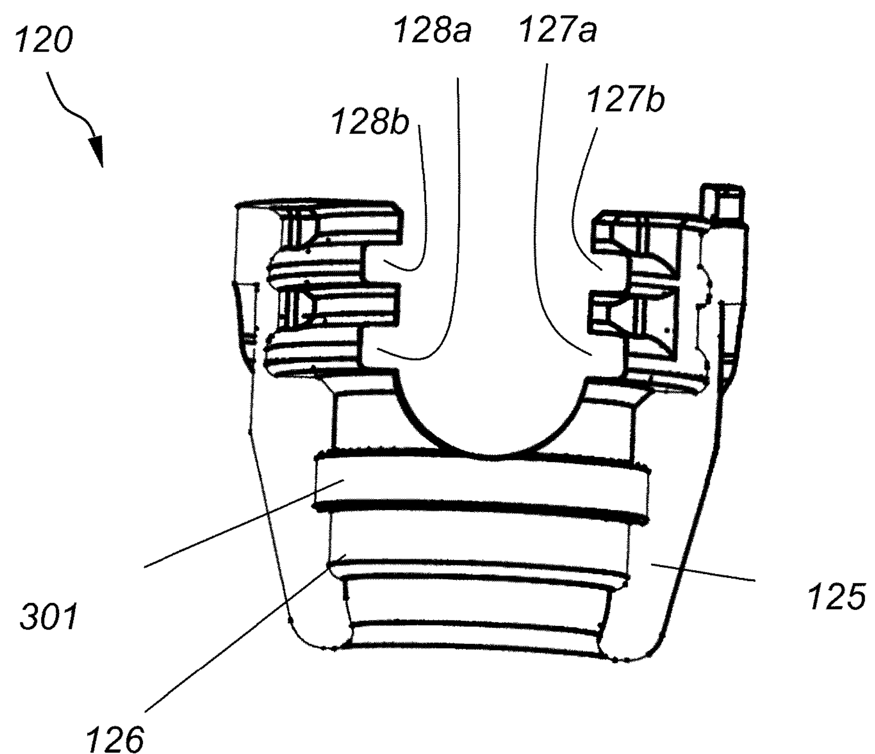
FIG. 33A is side cross-sectional view of the tulip-shaped head 120 of FIG. 32.
Figure 33B:
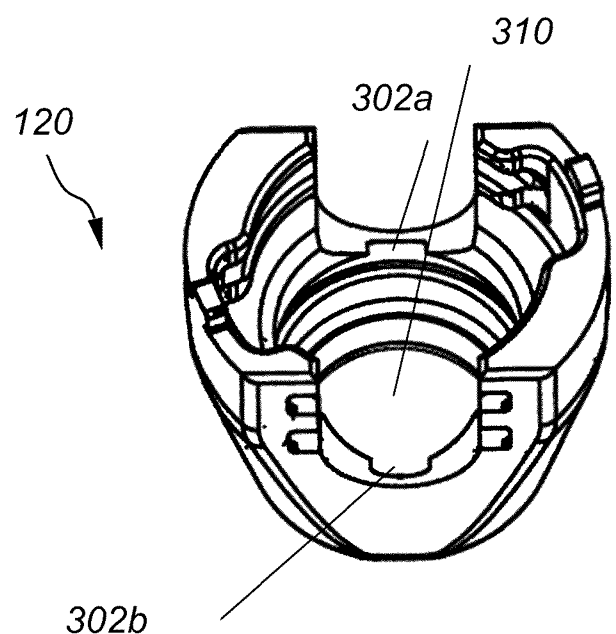
FIG. 33B is a top perspective view of the tulip-shaped head 120 of FIG. 32.
Figure 34:
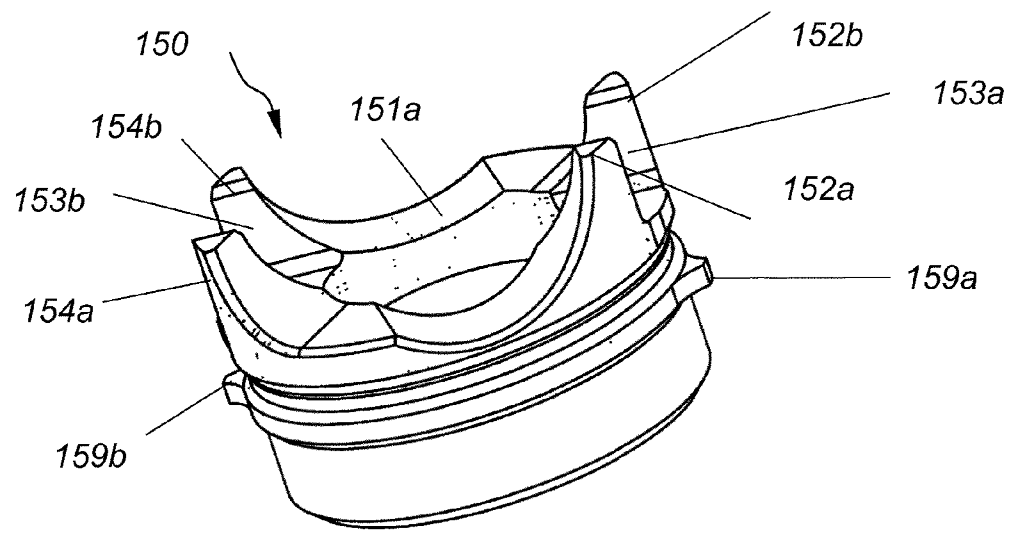
FIG. 34 is a side perspective view of the washer 150 of FIG. 32.
Figure 35:
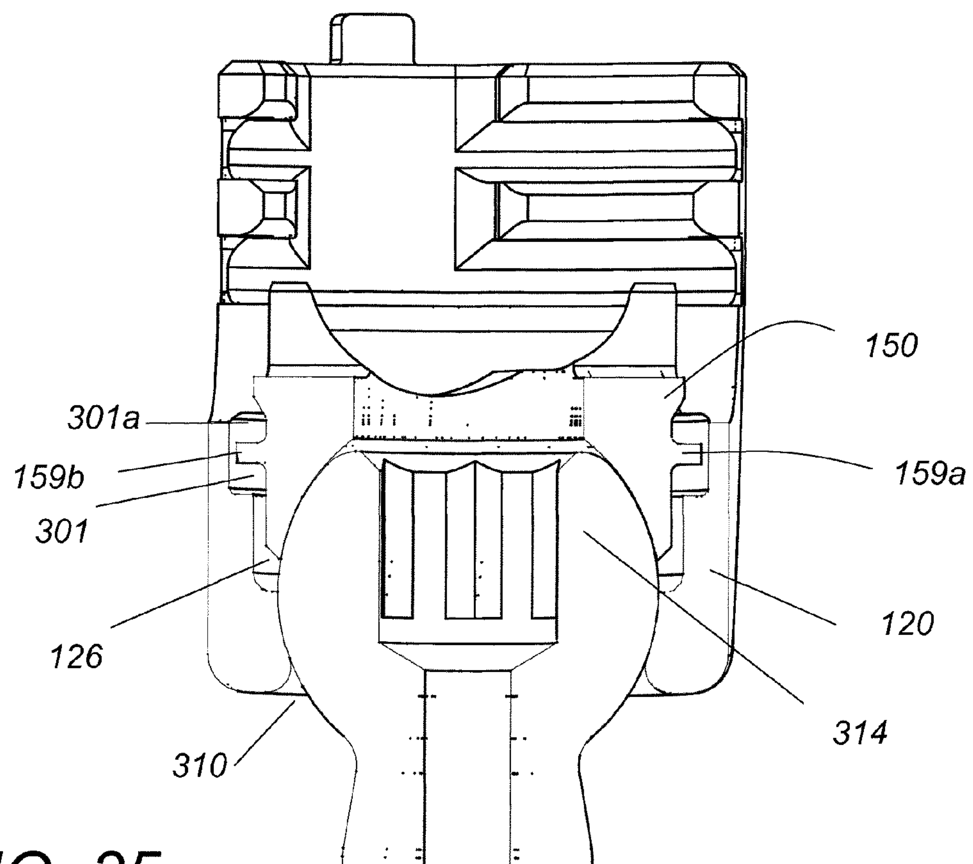
FIG. 35 is a side cross-sectional view of the spinal screw assembly of FIG. 32.

Referring to FIG. 31 and FIG. 32, another embodiment of the spinal screw assembly 300 includes an anchoring portion 310, a tulip-shaped head 120, a washer 150, a stabilization rod 130, a cap 140 and a locking element 160. The anchoring portion 310 is a screw having outer threads. The head 120 includes a base 125 and a U-shaped slot 122 dimensioned to receive the stabilization rod 130. The U-shaped slot 122 is formed by two legs 123, 124 extending from the base 125. Base 125 includes a groove 126 dimensioned to receive the washer 150, shown in FIG. 34. Referring to FIG. 34, washer 150 is cylindrically shaped and has a first set of wings 152*a*, 152*b* and a second set of wings 154*a*, 154*b*, extending upward from opposite edges of its top surface 151*a*. Wings 152*a*, 152*b* are dimensioned to engage a groove 127*a* formed in the inner lower portion of leg 123, shown in FIG. 33A. Wings 154*a*, 154*b* are dimensioned to engage a grove 128*a* formed in the inner lower portion of leg 124, shown in FIG. 33A. Wings 152*a*, 152*b* are separated by a slot 153*a* and wings 154*a*, 154*b* are separated by a slot 153*b*. Slots 153*a*, 153*b* are dimensioned to receive lower protrusions 142*a*, 142*b*, respectively, extending from the lower surface of cap 140, shown in FIG. 32. Washer 150 also includes side tabs 159*a*, 159*b* extending from opposite sides of its perimeter. Side tabs 159*a*, 159*b* interface with the upper lip 301*a* of annular groove 301 formed in the inner surface of base 125 and prevent the washer from being pushed out of the head 120 by the screw 310, as shown in FIG. 35. Annular groove 301 also includes two opposite loading cutouts 302*a*, 302*b*. The washer side tabs 159*a*, 159*b* are aligned with the cutouts 302*a*, 302*b*, respectively, when the washer is placed in the slot 122 and then the washer 150 is rotated so that the tabs are underneath the upper lip 301 of the annular groove 301. The top surface 151*a* of washer 150 also includes a groove 155 dimensioned to accommodate the stabilization rod 130 when the assembly is locked so that the groove axis 156 aligns parallel with the stabilization rod axis 132, as shown in FIG. 9. Cap 140 also includes upper protrusions 144*a*, 144*b* extending from the lower surface of cap 140 and formed above the lower protrusions 142*a*, 142*b*, respectively, as shown in FIG. 13 and FIG. 32. Upper protrusions 144*a*, 144*b* are dimensioned to engage grooves 127*b*, 128*b* formed in the inner upper portion of legs 123, 124, respectively. Cap 140 further includes a central bore 145 dimensioned to receive the locking element 160, which in this case is a threaded screw configured to engage inner threads in the bore 145, shown in FIG. 32. In this embodiment, screw 310 is not integral with the base 125 and includes a spherical head 314 dimensioned to sit in the base 125 while the threaded portion of the screw passes through a bore 310 formed in the base 125 of the head 120. This embodiment provides for multiaxial orientation of the screw 310 relative to the stabilization rod 130.

Figure 36A:
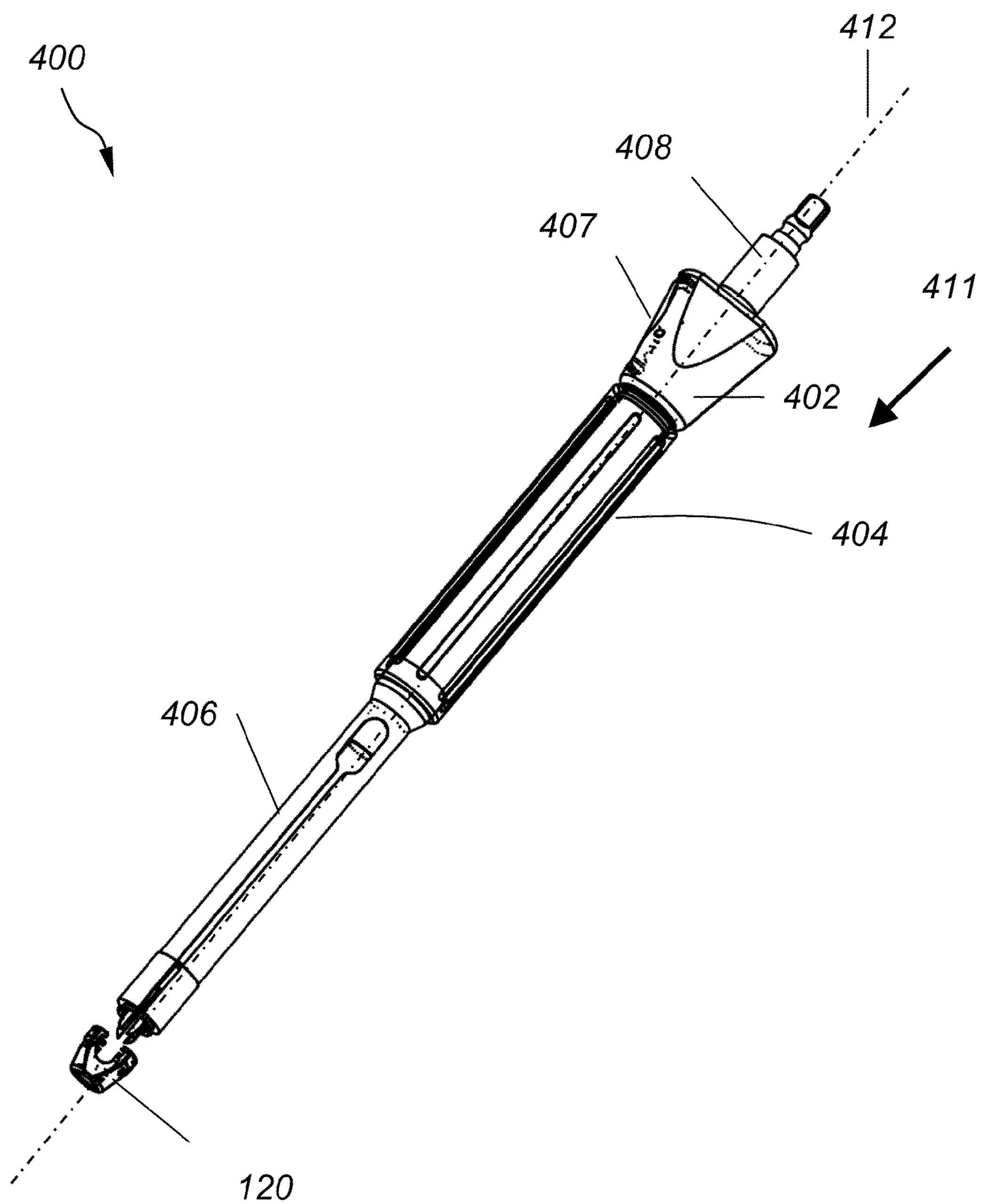
FIG. 36A is a perspective view of the inserter tool for the spinal screw assembly of FIG. 32.
Figure 36B:
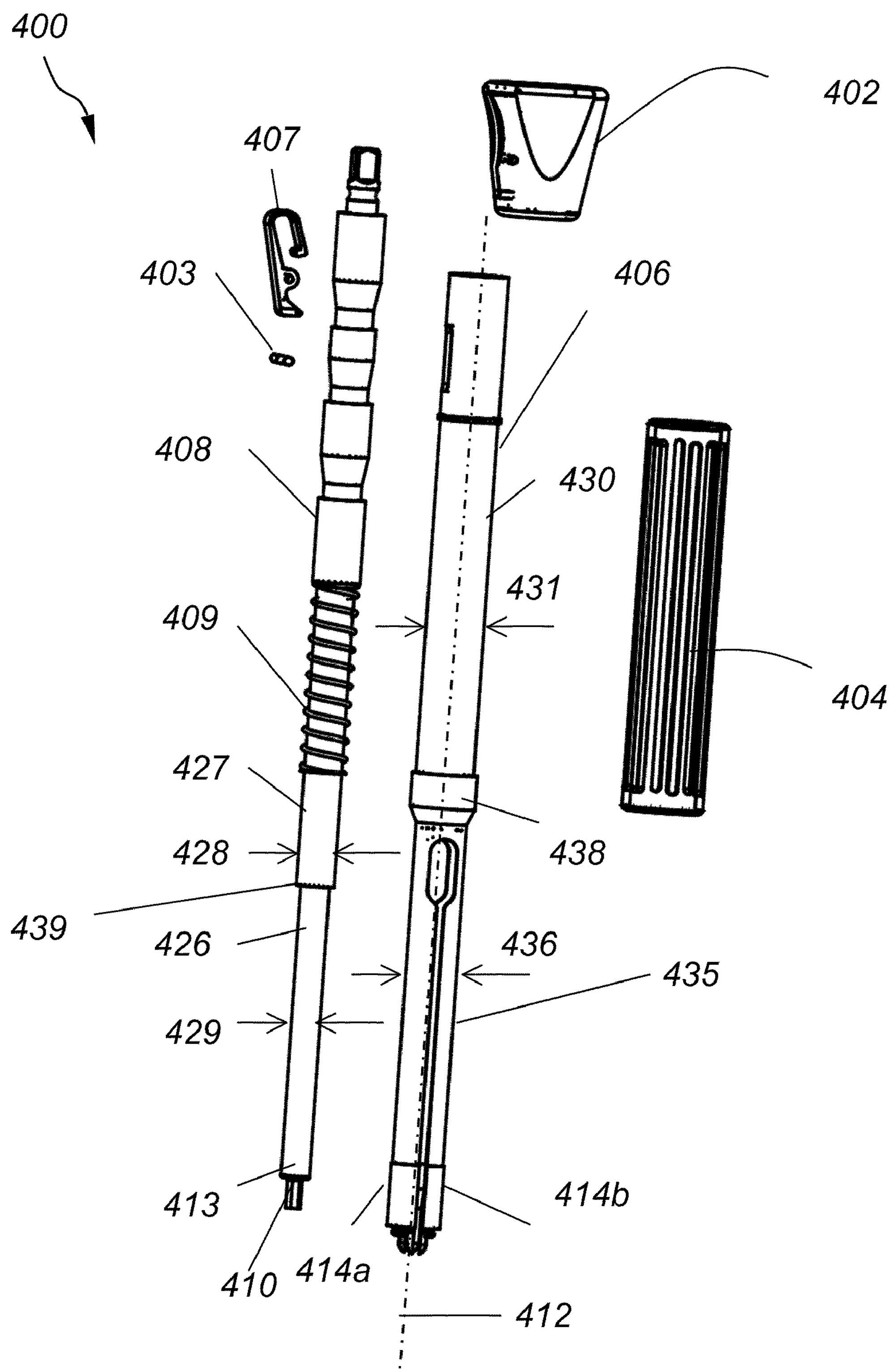
FIG. 36B is an exploded view of the inserter tool of FIG. 36A.
Figure 37A:
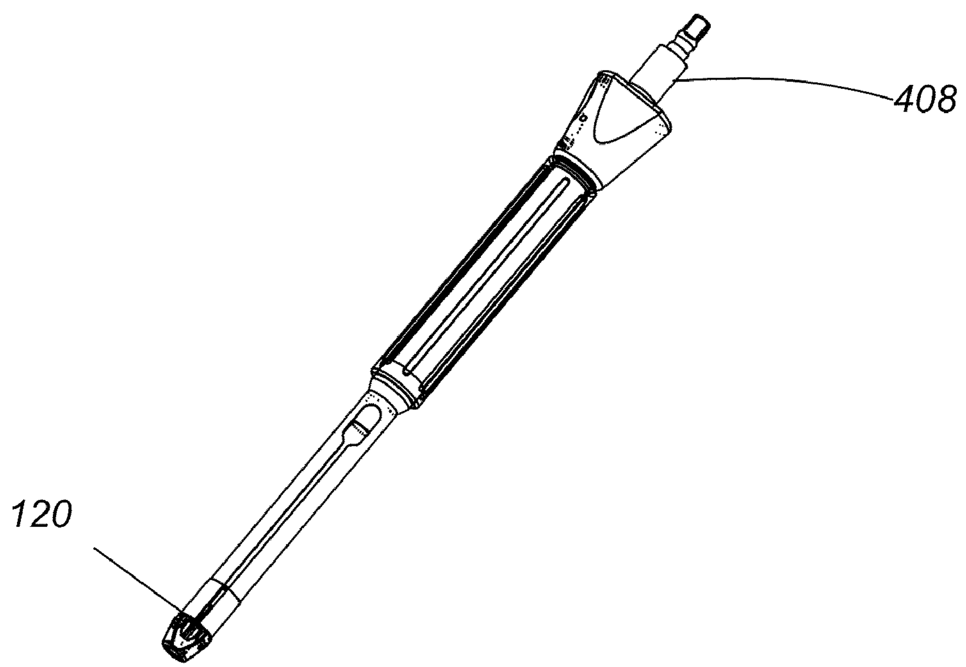
FIG. 37A depicts capturing the tulip-shaped screw head of FIG. 32 with the inserter tool of FIG. 36A.
Figure 37B:
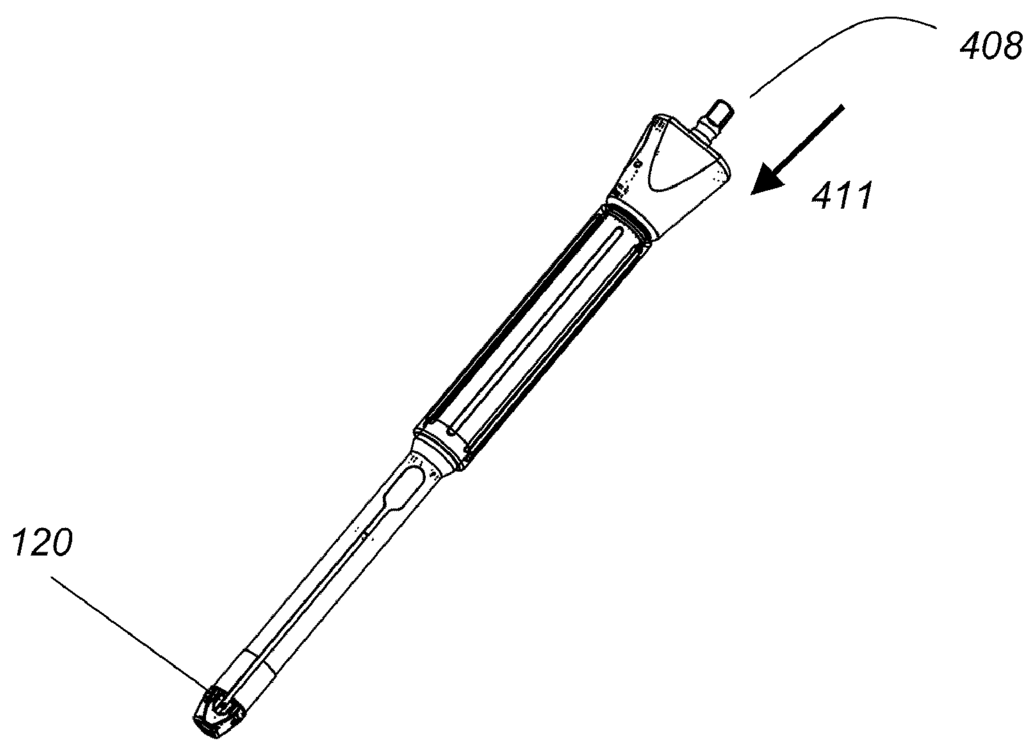
FIG. 37B depicts locking the tulip-shaped screw head of FIG. 32 onto the inserter tool of FIG. 36A.
Figure 38A:
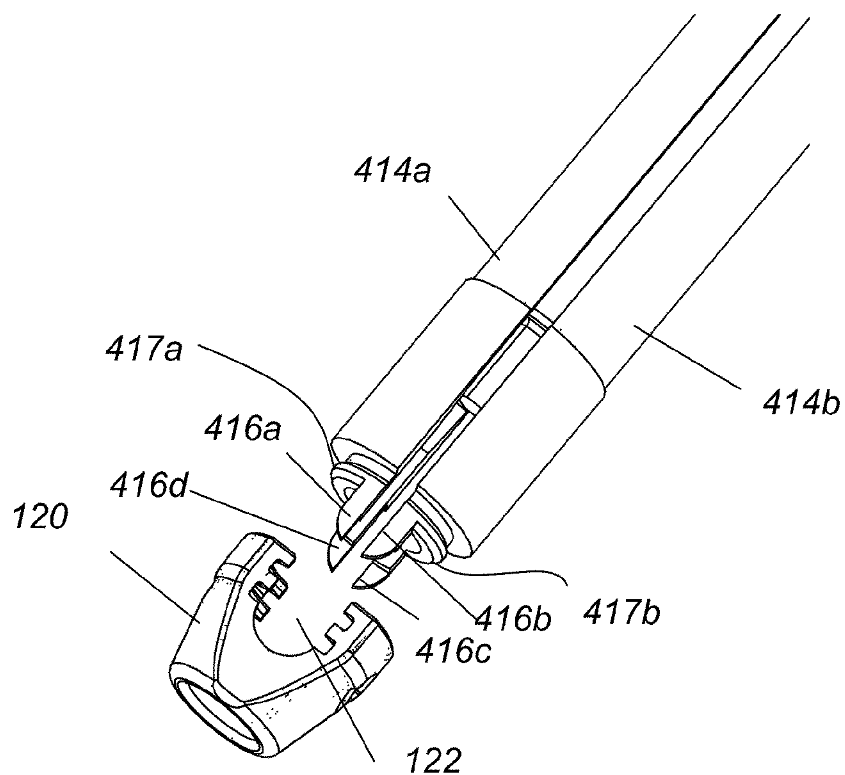
FIG. 38A is a detailed view of the inserter tool end portion prior to engaging the tulip-shaped screw head.
Figure 38B:
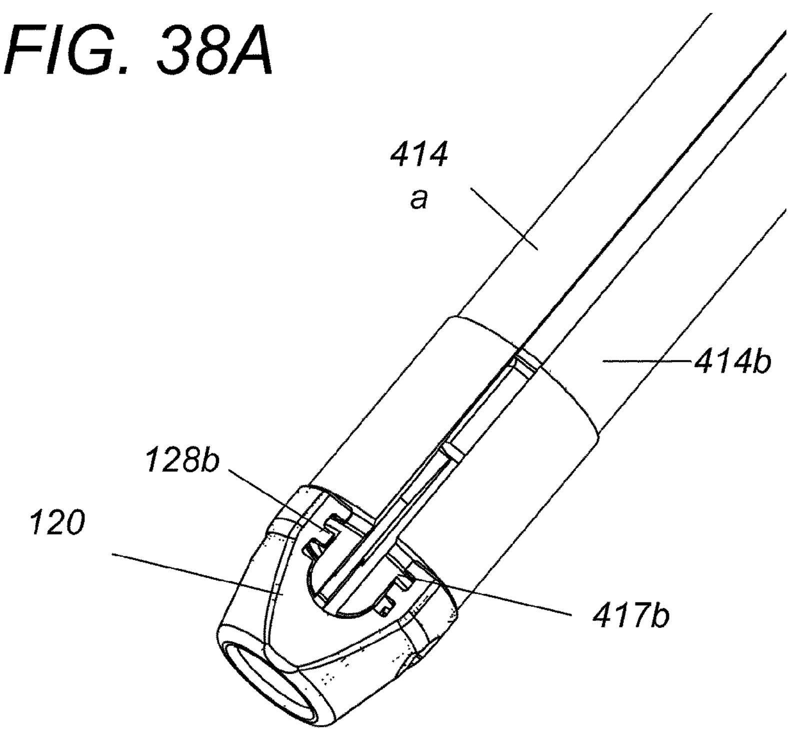
FIG. 38B is a detailed view of the inserter tool end portion with the engaged tulip-shaped screw head.
Figure 38C:
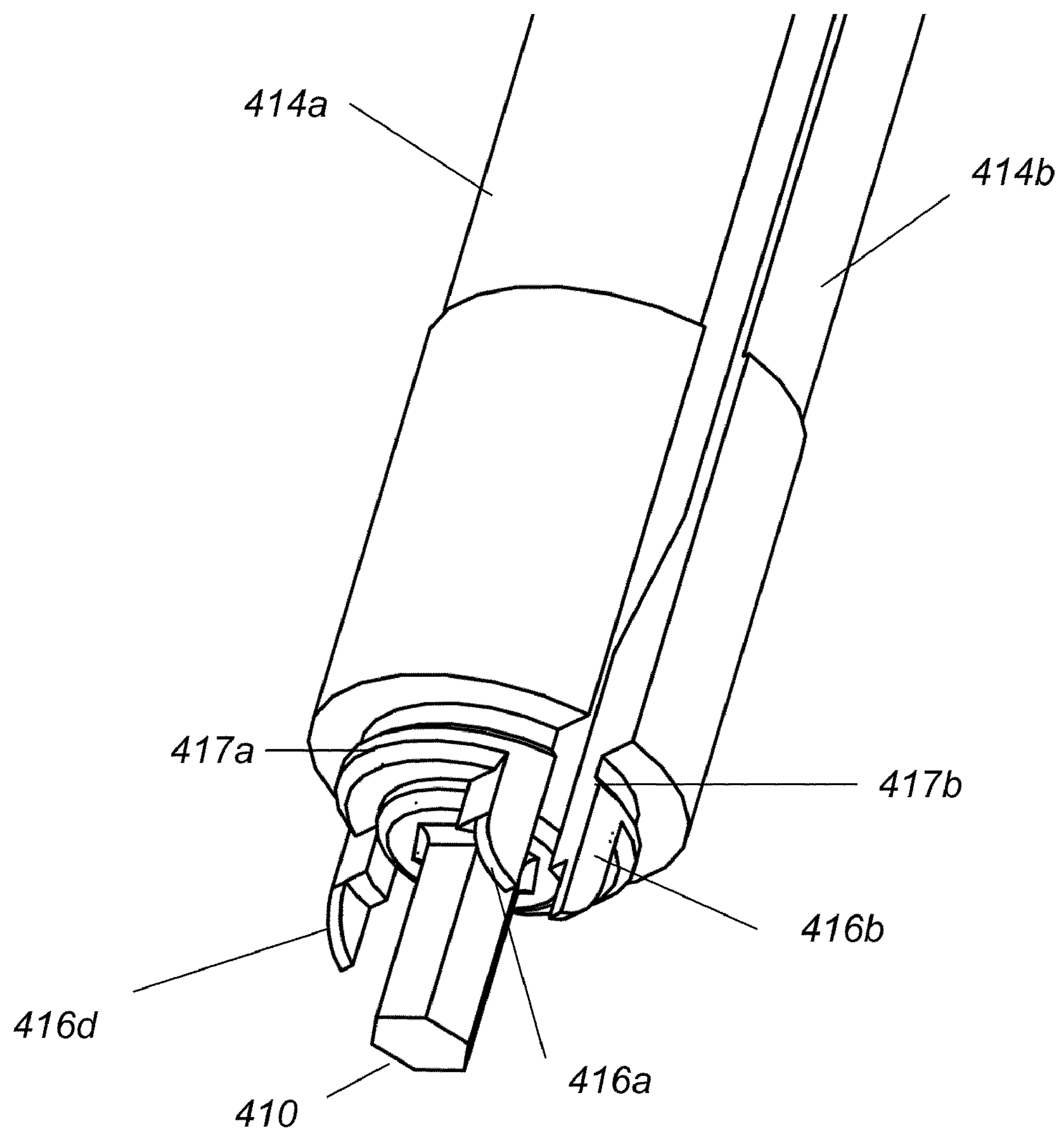
FIG. 38C is a detailed view of the inserter tool end portion with the screwdriver tip pushed down.
Figure 39A:
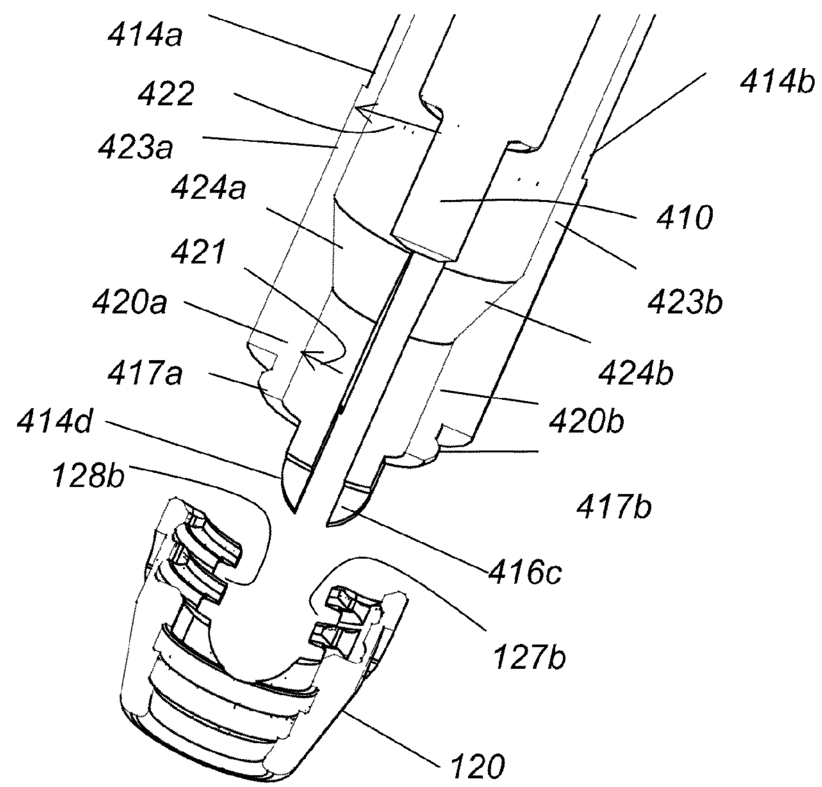
FIG. 39A is a detailed cross-sectional view of the inserter tool end portion prior to engaging the tulip-shaped screw head.
Figure 39B:
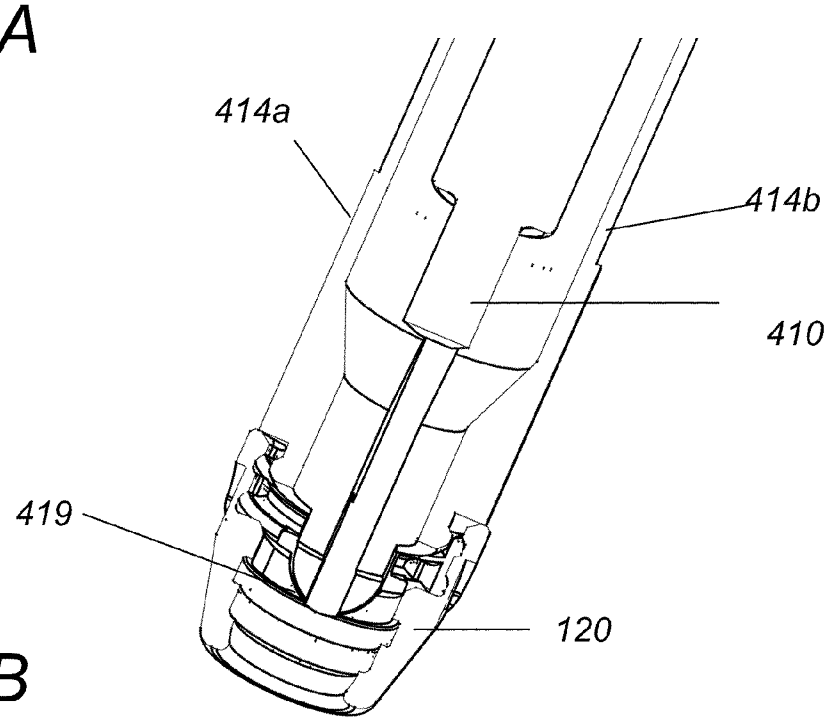
FIG. 39B is a detailed cross-sectional view of the inserter tool end portion inserted into the tulip-shaped screw head.
Figure 39C:
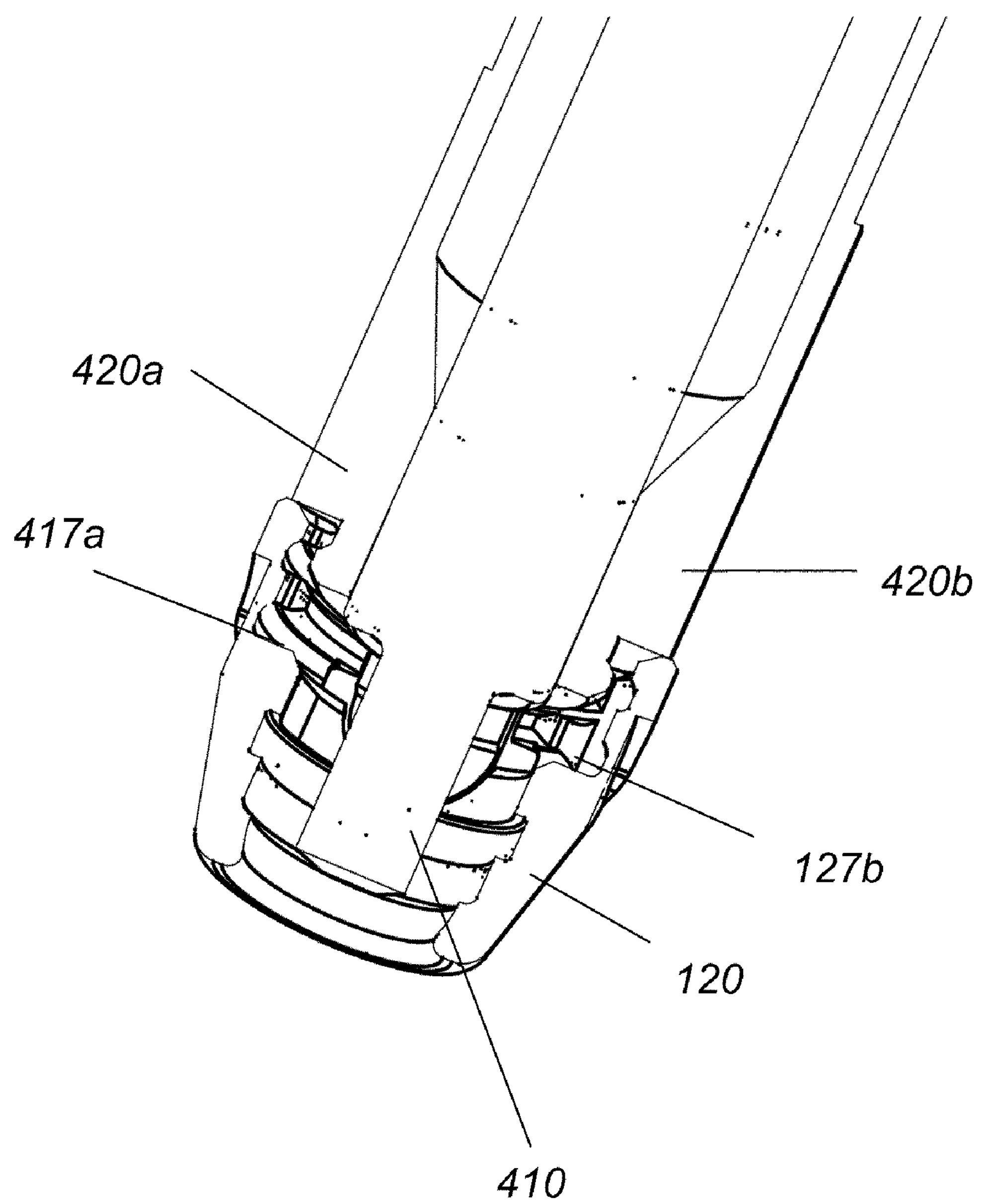
FIG. 39C is a detailed cross-sectional view of the inserter tool end portion inserted into the tulip-shaped screw head and with the screwdriver tip pushed down.

An inserter tool is used for capturing the screw assembly 300 and placing the screw 310 into a desired vertebral location. Referring to FIG. 36A and FIG. 36B the inserter tool 400 includes a handle 402 and an elongated cylindrical driver shaft 408 surrounded by a hollow cylindrical retention sleeve 406. An outer sleeve 404 surrounds the retention sleeve 406. The elongated driver shaft includes an upper portion 427, a lower portion 426 and a distal end 413. The diameter 428 of the upper portion 427 of the diver shaft 408 is larger than the diameter 429 of the lower portion 426 of the driver shaft 408 and a step 439 is formed between the upper 427 and the lower portion 426 of the driver shaft 408. The distal end 413 of the driver shaft 408 has a tip 410 extending from it. The diameter of the tip 410 is smaller than the diameter of the rest of the driver shaft and is dimensioned and shaped to interface and engage with the opening 161 of the locking element 160 and/or the opening 315 at the top of the screw head 314. In one example, the tip 410 has a hexagonal shape, as shown in FIG. 38C. In other examples, tip 410 may be rectangular, conical, or crossed-shaped. The screw-engaging tip 410 engages the screw head 134 or the locking element 160 so that when the driver shaft 408 is rotated clockwise or counter-clockwise, the screw 310 or the locking element 160 is advanced or retracted to or from the desired location, respectively. The retention sleeve 406 includes an upper portion 430 and a lower portion 435. A central elongated opening extends along direction 412 of the retention sleeve and is dimensioned to house the driver shaft 408. The diameter 431 of the upper portion 430 of the retention sleeve 406 is larger than the diameter 436 of the lower portion 435 of the retention sleeve 406. A step 438 is formed in the transition between the upper 430 and lower portion 435 of the retention sleeve 406. The upper portion 427 of the driver shaft 408 is dimensioned to be accommodated within the upper portion 430 of the sleeve 406 and to be prevented from entering into the lower portion 435 of the sleeve 406. The driver shaft 408 is configured to move in the direction of arrow 411, as shown in FIG. 37B. A spring 409 surrounds the upper portion 427 of the driver shaft 408 and is compressed against the inner surface of step 438 when the driver shaft 408 is pushed down in the direction 411. The position of the driver shaft 408 within the upper portion 430 of the retention sleeve 406 is locked with a pawl 407 which is secured within the handle 402. The lower portion 435 of the retention sleeve 406 is slotted and includes two parallel flexible half-cylindrical hollow segments 414*a*, 414*b*, as shown in FIG. 38A. The distal ends 420*a*, 420*b* of segments 414*a*, 414*b* have an inner radius 421 that is smaller than the inner radius 422 of the main portions 423*a*, 423*b* of the segments 414*a*, 414*b*, as shown in FIG. 39A. The transition portions 424*a*, 424*b* between the main portions 423*a*, 423*b* of each segment to the distal ends 420*a*, 420*b* have the shape of a truncated cone, as shown in FIG. 39A. Segment 414*a* includes a half-annular ridge 417*a* extending around the outer surface of the distal end 420*a* and two elongated protrusions 416*a*, 416*d* extending from the bottom surface of the distal end 420*a*. Similarly segment 414*b* includes elongated protrusions 416*b*, 416*c* extending from the bottom surface of its distal end 420*b* and a half-annular ridge 417*b* extending around the outer surface of the distal end 420*b*. Distal ends 420*a*, 420*b* are inserted into opening 122 of the tulip-shaped head 120 and half annular ridges 417*a*, 417*b* interface with grooves 127*b*, 128*b* of the tulip-shaped head 120 to engage the driver shaft 408 onto the tulip-shaped head 120. Protrusions 416*a*-416*d* have curved outer edges 419 configured to interface with the curvature of the inner walls of opening 122, as shown in FIG. 39B. The diameter of the driver shaft lower portion is slightly larger than the diameter of the lower portion of the retention sleeve. When the instrument is at rest, pawl 407 is locked and the distal ends 420*a*, 420*b* of segments 414*a*, 414*b* of the retention sleeve 406 are pinched together. In operation the distal ends 420*a*, 420*b* of the inserter 400 are placed into opening 122 of the tulip shaped head 120 of the screw assembly 300, as shown in FIG. 37A and FIG. 39B. Next, the pawl 407 is released and the driver shaft 408 is pushed down in the direction of arrow 411. Pushing the driver shaft 408 down causes the distal ends 420*a*, 420*b* of segments 417*a*, 417*b* to expand within the opening 122 of the head 120, respectively, and inserts the tip 410 of the driver 408 into the opening 315 of the screw head 314. The expansion of segments 417*a*, 417*b* interlocks annular ridges 417*a*-417*b* within the annular grooves 127*b*, 128*b* of the tulip-shaped head 120 and this locks the head 120 onto the distal ends 420*a*, 420*b* of the inserter tool, as shown in FIG. 37B an FIG. 39C. Once the distal ends 420*a*, 420*b* of the inserter tool is locked onto the tulip-shaped head 120, the pawl 407 is locked again to prevent accidental disengagement. The reverse procedure is followed in order to remove the inserter tool 400 from the tulip-shaped head 120. Unlocking the pawl 407 and withdrawing the driver shaft 408 in the opposite direction of 411 brings segments 417*a*, 417*b* together and disengages the distal ends 420*a*, 420*b* from the tulip-shaped head 120.

Other embodiments are within the scope of the following claims. The screw assembly is made of metal, plastic, ceramic, bone, polymers, composites, absorbable material, biodegradable material, or combinations thereof. The insertion toll is made of metal, alloy or composite material.

Several embodiments of the present invention have been described. Nevertheless, it will be understood that various modifications may be made without departing from the spirit and scope of the invention. Accordingly, other embodiments are within the scope of the following claims.

What is claimed is:

1. A bone screw assembly comprising:

a tulip-shaped seat comprising a semispherical bottom portion and a cylindrical side portion extending upward from said bottom portion and wherein said bottom portion comprises a through opening dimensioned to receive a bone fixation device and to prevent the fixation device from passing entirely therethrough and wherein said side portion comprises first and second concentric grooves extending along its inside periphery wall and a horizontal channel dimensioned to receive a rod;

a bone fixation device comprising a bone fixation portion passing through said bottom portion opening and a head residing within said semispherical bottom portion;

a ring-shaped washer placed into said seat on top of said bone fixation device head and comprising a first pair of outward extending projections separated by a first gap and a second pair of outward extending projections separated by a second gap, wherein said projections extend from the top surface of said washer and are shaped and dimensioned to interface with said first concentric groove of said seat side portion;

a rod placed within said channel and positioned within a groove formed on the top surface of said washer;

and a cap comprising first and second projections extending downward from its bottom surface and wherein each of said first and second downward projections comprises first and second sidewise extending ridges and wherein said first ridges of said first and second projections are aligned and placed within said first and second gaps of said washer, respectively, and interface with said first groove of said seat side portion and said second ridges interface with said second groove of said seat side portion when the cap is rotate.

2. The bone screw assembly of claim 1 wherein said bone fixation device comprises a polyaxial screw.

3. The bone screw assembly of claim 1 further comprising a locking screw threaded through a central opening formed in said cap for locking said rod down onto said bone fixation head.

4. A bone screw assembly comprising:

a tulip-shaped seat comprising a semispherical bottom portion, a cylindrical side portion extending upward from said bottom portion and a bone fixation device extending downward from the bottom portion and wherein said side portion comprises first and second concentric grooves extending along its inside periphery wall and a horizontal channel dimensioned to receive a rod;

a ring-shaped washer placed into said seat on top of said head of said bone fixation device and comprising a first pair of outward extending projections separated by a first gap and a second pair of outward extending projections separated by a second gap, wherein said projections extend from the top surface of said washer and are shaped and dimensioned to interface with said first concentric groove of said seat side portion;

a rod placed within said channel and positioned within a groove formed on the top surface of said washer; and a cap comprising first and second projections extending downward from its bottom surface and wherein each of said first and second downward projections comprises first and second sidewise extending ridges and wherein said first ridges of said first and second projections are aligned and placed within said first and second gaps of said washer, respectively, and interface with said first groove of said seat side portion and said second ridges interface with said second groove of said seat side portion when the cap is rotate.

5. A bone screw assembly comprising:

a tulip-shaped seat comprising a semispherical bottom portion and a cylindrical side portion extending upward from said bottom portion and wherein said bottom portion comprises a through opening dimensioned to receive a bone fixation device and to prevent the fixation device from passing entirely therethrough and wherein said side portion comprises first and second side through openings arranged opposite to each other and on opposite sides of said side portion and a horizontal channel dimensioned to receive a rod;

a bone fixation device comprising a bone fixation portion passing through said bottom portion opening and a head residing within said semispherical bottom portion;

a cylindrically-shaped washer placed into said seat on top of said bone fixation device head and comprising a first and second outward extending side projections, wherein said side projections extend from the opposite sides of said washer side surface and are shaped and dimensioned to interface with said first and second side through openings of said seat, respectively and to protrude through the outer surface of said seat side portion;

a rod placed within said channel and positioned within a groove formed on the top surface of said washer; and a cap comprising first and second sides extending downward from its bottom surface and wherein said first and second sides comprise first and second grooves, respectively, and wherein said first and second grooves of said first and second sides are aligned and placed around the outer surface of said seat side portion, and interface with said first and second side projection protruding through said first and second side through openings when the cap is rotate.

6. The bone screw assembly of claim 5 wherein said bone fixation device comprises a polyaxial screw.

7. The bone screw assembly of claim 5 further comprising a locking screw threaded through a central opening formed in said cap for locking said rod down onto said bone fixation head.

8. A bone screw assembly comprising:

a tulip-shaped seat comprising a semispherical bottom portion and a cylindrical side portion extending upward from said bottom portion and wherein said bottom portion comprises a groove extending along its inside periphery wall and a through opening dimensioned to receive a bone fixation device and to prevent the fixation device from passing entirely therethrough and wherein said side portion comprises first and second concentric grooves extending along its inside periphery wall and a horizontal channel dimensioned to receive a rod;

a bone fixation device comprising a bone fixation portion passing through said bottom portion opening and a head residing within said semispherical bottom portion;

a cylindrically-shaped washer placed into said seat on top of said bone fixation device head and comprising first and second side tabs and a first pair of upward extending projections separated by a first gap and a second pair of upward extending projections separated by a second gap, wherein said projections extend from the top surface of said washer and wherein said first and second side tabs extend from opposite external side wall of said washer and interface with said bottom portion groove;

a rod placed within said channel and positioned within a groove formed on the top surface of said washer; and a cap comprising first and second projections extending downward from its bottom surface and wherein each of said first and second downward projections comprises first and second sidewise extending ridges and wherein said first ridges of said first and second projections are aligned and placed within said first and second gaps of said washer, respectively, and interface with said first groove of said side portion of the seat and said second ridges interface with said second groove of said side portion of the seat when the cap is rotate.

9. The bone screw assembly of claim 8 wherein said bone fixation device comprises a polyaxial screw.

10. The bone screw assembly of claim 8 further comprising a locking screw threaded through a central opening formed in said cap for locking said rod down onto said bone fixation head.

11. An inserter tool for a bone screw assembly comprising a bone screw and a tulip-shaped seat said inserter tool comprising:

a driver shaft comprising an elongated cylindrical body having a screw engaging distal end and wherein said cylindrical body comprises upper and lower portions and wherein said upper portion has a diameter larger than the diameter of the lower portion;

a retention sleeve surrounding said driver shaft body and comprising a hollow cylindrical body having an upper portion, a lower portion and an intermediate step portion wherein said upper portion has a diameter larger than the diameter of the lower portion and is dimensioned to house said driver shaft upper portion and said lower portion is dimensioned to house said driver shaft lower portion and wherein said sleeve lower portion comprises first and second flexible parallel segments;

a spring surrounding said driver shaft upper portion and wherein said driver shaft is configured to be pushed down or pulled up and slide within said retention sleeve and compress said spring against said step portion;

a pawl configured to lock the position of the driver shaft relative to the retention sleeve;

wherein said first and second flexible segments comprise first and second distal ends, respectively, configured to engage said tulip-shaped seat.

12. The inserter tool of claim 11 wherein each of said distal ends comprises a half annular ridge and first and second elongated protrusions extending downward from the bottom surface of the distal end and wherein said annular ridge interfaces with an annular groove formed in said tulip-shaped seat and said first and second protrusions interface with the walls of a U-shaped opening formed in the tulip-shaped seat.

13. The inserter tool of claim 12 wherein said driver shaft lower portion comprises a diameter larger than the diameter of the lower portion of the retention sleeve and wherein pushing the driver shaft down flexes said first and second flexible segments outward and locks said side annular ridges into said annular groove, thereby locking said tulip-shaped seat onto said first and second distal ends.

14. The inserter tool of claim 11 further comprising an outer sleeve surrounding said retention sleeve.

15. The inserter tool of claim 11 further comprising a handle.

* * * * *